US009795750B2

(12) United States Patent
Bilgic

(10) Patent No.: US 9,795,750 B2
(45) Date of Patent: Oct. 24, 2017

(54) DRY POWDER INHALER

(71) Applicant: Sima Patent ve Lisanslama Hizmetleri Ltd. Sti., Esenler/Istanbul (TR)

(72) Inventor: Mahmut Bilgic, Istanbul (TR)

(73) Assignee: Sima Patent ve Lisanslama Hizmetleri Ltd. Sti., Esenler/Istanbul (TR)

( * ) Notice: Subject to any disclaimer, the term of this patent is extended or adjusted under 35 U.S.C. 154(b) by 269 days.

(21) Appl. No.: 14/695,726

(22) Filed: Apr. 24, 2015

(65) Prior Publication Data

US 2015/0231345 A1    Aug. 20, 2015

Related U.S. Application Data

(60) Division of application No. 13/451,838, filed on Apr. 20, 2012, now Pat. No. 9,345,848, which is a
(Continued)

(30) Foreign Application Priority Data

| Oct. 20, 2009 | (TR) | 2009 07917 |
| Apr. 13, 2010 | (TR) | 2010 02877 |
| Apr. 20, 2010 | (TR) | 2010 03091 |
| Apr. 26, 2010 | (TR) | 2010 03238 |
| May 28, 2010 | (TR) | 2010 04307 |

(Continued)

(51) Int. Cl.
*A61M 15/00* (2006.01)

(52) U.S. Cl.
CPC .... *A61M 15/0046* (2014.02); *A61M 15/0025* (2014.02); *A61M 15/0071* (2014.02); *A61M 2202/064* (2013.01); *A61M 2205/19* (2013.01)

(58) Field of Classification Search
CPC .......... A61M 15/0003; A61M 15/0006; A61M 15/0008; A61M 15/0013; A61M 15/0016;
(Continued)

(56) References Cited

U.S. PATENT DOCUMENTS

| 2,625,292 A | 1/1953 | Spender |
| D335,029 S | 4/1993 | Gerding |

(Continued)

FOREIGN PATENT DOCUMENTS

| CA | 2544745 A1 | 5/2005 |
| EP | 1175220 A2 | 1/2002 |

(Continued)

OTHER PUBLICATIONS

International Search Report and Written Opinion for International Application No. PCT/TR2011/000085 dated Aug. 10, 2011 (10 pages).
(Continued)

*Primary Examiner* — Annette Dixon
(74) *Attorney, Agent, or Firm* — Clark & Elbing LLP

(57) ABSTRACT

The present invention relates to an inhaler which is appropriate for delivery of medicament in dry powder form used in respiratory diseases, particularly in asthma and chronic obstructive pulmonary disease (COPD). In addition, the present invention relates to an inhaler which includes a blister package appropriate for carrying the medicament in dry powder form and used to realize an effective inhalation.

13 Claims, 29 Drawing Sheets

Related U.S. Application Data continuation-in-part of application No. PCT/TR2011/000091, filed on Apr. 13, 2011, and a continuation-in-part of application No. PCT/TR2011/000094, filed on Apr. 13, 2011, and a continuation-in-part of application No. PCT/TR2011/000089, filed on Apr. 13, 2011, and a continuation-in-part of application No. PCT/TR2011/000093, filed on Apr. 13, 2011, and a continuation-in-part of application No. PCT/TR2011/000085, filed on Apr. 13, 2011, and a continuation-in-part of application No. PCT/TR2011/000088, filed on Apr. 13, 2011, and a continuation-in-part of application No. PCT/TR2011/000087, filed on Apr. 13, 2011, and a continuation-in-part of application No. PCT/TR2011/000095, filed on Apr. 13, 2011, and a continuation-in-part of application No. PCT/TR2011/000086, filed on Apr. 13, 2011, and a continuation-in-part of application No. PCT/TR2011/000090, filed on Apr. 13, 2011, and a continuation-in-part of application No. PCT/TR2010/000210, filed on Oct. 20, 2010.

(30) Foreign Application Priority Data

| Date | | Number |
|---|---|---|
| May 28, 2010 | (TR) | 2010 04308 |
| May 28, 2010 | (TR) | 2010 04310 |
| May 28, 2010 | (TR) | 2010 04312 |
| May 28, 2010 | (TR) | 2010 04313 |
| May 28, 2010 | (TR) | 2010 04317 |

(58) Field of Classification Search
CPC ......... A61M 15/0025; A61M 15/0026; A61M 15/0028; A61M 15/0031; A61M 15/0033; A61M 15/0036; A61M 15/0041; A61M 15/0043; A61M 15/0045; A61M 15/0048; A61M 15/0051; A61M 15/0055; A61M 15/006; A61M 15/0066; A61M 15/007; A61M 15/0075; A61M 15/0078; A61M 15/0085; A61M 15/0086; A61M 15/0091; A61M 15/02; A61M 2016/0024; A61M 2202/064; A61M 2205/073; A61M 2205/12; A61M 2205/123; A61M 2205/14; A61M 2205/18; A61M 2205/582; A61M 2205/583; A61M 2205/8206; A61M 2206/16
USPC ............ 128/202.22, 203.12, 203.15, 203.21
See application file for complete search history.

(56) References Cited

U.S. PATENT DOCUMENTS

| | | | |
|---|---|---|---|
| 5,657,749 | A | 8/1997 | Cox |
| 6,092,522 | A | 7/2000 | Calvert et al. |
| 6,234,365 | B1 | 5/2001 | Bougamont et al. |
| D450,117 | S | 11/2001 | Braithwaite et al. |
| D479,689 | S | 9/2003 | Altonen et al. |
| 6,880,555 | B1 * | 4/2005 | Brunnberg ......... A61M 15/0045 128/203.12 |
| D505,865 | S | 6/2005 | Seizer et al. |
| D518,171 | S | 3/2006 | Anderson et al. |
| D590,495 | S | 4/2009 | Lulla et al. |
| D590,938 | S | 4/2009 | Lulla et al. |
| D613,397 | S | 4/2010 | Nakao et al. |
| 7,694,676 | B2 | 4/2010 | Wachtel |
| D641,890 | S | 7/2011 | Nardo |
| D645,734 | S | 9/2011 | Eason et al. |
| D683,844 | S | 6/2013 | Andrade et al. |
| D710,002 | S | 7/2014 | Valentine et al. |
| 2002/0132001 | A1 | 9/2002 | Garthwaite et al. |
| 2003/0172927 | A1 | 9/2003 | Young et al. |
| 2004/0094152 | A1 | 5/2004 | Harvey et al. |
| 2004/0173211 | A1 | 9/2004 | Kladders et al. |
| 2005/0005934 | A1 | 1/2005 | Harvey |
| 2005/0154491 | A1 | 7/2005 | Anderson et al. |
| 2005/0172964 | A1 | 8/2005 | Anderson et al. |
| 2005/0268909 | A1 | 12/2005 | Bonney et al. |
| 2005/0279357 | A1 | 12/2005 | Wachtel |
| 2006/0196504 | A1 | 9/2006 | Augustyn et al. |
| 2007/0062525 | A1 | 3/2007 | Bonney et al. |
| 2008/0196718 | A1 | 8/2008 | Connell et al. |
| 2008/0308102 | A1 | 12/2008 | Davies et al. |
| 2009/0078252 | A1 | 3/2009 | Anderson et al. |
| 2009/0139516 | A1 | 6/2009 | Augustyn et al. |
| 2010/0000528 | A1 | 1/2010 | Palmer et al. |
| 2010/0000529 | A1 | 1/2010 | Prime et al. |
| 2010/0059052 | A1 | 3/2010 | Davies et al. |
| 2011/0232637 | A1 | 9/2011 | Kaemper et al. |
| 2011/0271958 | A1 | 11/2011 | Sawant |
| 2012/0260917 | A1 | 10/2012 | Bilgic |
| 2014/0318538 | A1 | 10/2014 | Bilgic |
| 2015/0231345 | A1 | 8/2015 | Bilgic |
| 2015/0231346 | A1 | 8/2015 | Bilgic |

FOREIGN PATENT DOCUMENTS

| | | |
|---|---|---|
| EP | 2082759 A1 | 7/2009 |
| EP | 2082764 A1 | 7/2009 |
| GB | 1459426 A | 12/1976 |
| GB | 2407042 A | 4/2005 |
| GB | 2447560 A | 9/2008 |
| WO | WO-00/33847 A1 | 6/2000 |
| WO | WO-01/41770 A2 | 6/2001 |
| WO | WO-02/36189 A1 | 5/2002 |
| WO | WO-03/095010 A2 | 11/2003 |
| WO | WO-2006/066908 A1 | 6/2006 |
| WO | WO-2007/012960 A1 | 2/2007 |
| WO | WO-2008/074098 A1 | 6/2008 |
| WO | WO-2009/003989 A1 | 1/2009 |
| WO | WO-2009/139731 A1 | 11/2009 |
| WO | WO-2011/133740 A1 | 10/2011 |

OTHER PUBLICATIONS

International Search Report and Written Opinion for International Application No. PCT/TR2011/000086, mailed Oct. 6, 2011 (8 pages).

International Search Report and Written Opinion for International Application No. PCT/TR2011/000087 mailed Aug. 18, 2011 (8 pages).

International Search Report and Written Opinion for International Application No. PCT/TR2011/000088 mailed Oct. 6, 2011 (8 pages).

International Search Report and Written Opinion for International Application No. PCT/TR2011/000089 mailed Jul. 22, 2011 (9 pages).

International Search Report and Written Opinion for International Application No. PCT/TR2011/000090 mailed Aug. 22, 2011 (8 pages).

International Search Report and Written Opinion for International Application No. PCT/TR2011/000091 mailed Jul. 29, 2011 (9 pages).

International Search Report and Written Opinion for International Application No. PCT/TR2011/000093 mailed Jul. 21, 2011 (9 pages).

International Search Report and Written Opinion for International Application No. PCT/TR2011/000094 mailed Sep. 28, 2011 (9 pages).

International Search Report and Written Opinion for International Application No. PCT/TR2011/000095 mailed Aug. 4, 2011 (9 pages).

(56) References Cited

OTHER PUBLICATIONS

International Search Report and Written Opinion for International Application No. PCT/TR2011/000210 mailed Mar. 7, 2012 (7 pages).

* cited by examiner

DRY POWDER INHALER

CROSS-REFERENCE TO RELATED APPLICATIONS

This application is a division of U.S. application Ser. No. 13/451,838, filed Apr. 20, 2012, now U.S. Pat. No. 9,345,848, which is a continuation-in-part of PCT Application No. PCT/TR2010/000210, filed Oct. 20, 2010, and PCT Application Nos. PCT/TR2011/000085, PCT/TR2011/000086, PCT/TR2011/000087, PCT/TR2011/000088, PCT/TR2011/000089, PCT/TR2011/000090, PCT/TR2011/000091, PCT/TR2011/000093, PCT/TR2011/000094, and PCT/TR2011/000095, filed Apr. 13, 2011, each of which is incorporated herein by reference in its entirety. U.S. application Ser. No. 13/451,838 also claims priority to Turkish patent applications TR2009/07917, filed Oct. 20, 2009, TR2010/02877, filed Apr. 13, 2010, TR2010/03091, filed Apr. 20, 2010, TR2010/03238, filed Apr. 26, 2010, TR2010/04307, TR2010/04308, TR2010/04310, TR2010/04312, TR2010/04313, and TR2010/04317, filed May 28, 2010.

BACKGROUND OF THE INVENTION

It is rather common to use inhalers for delivering medicaments utilized in the treatment and prophylaxis of respiratory diseases. Inhalation treatment is the most commonly preferred treatment method in these diseases as the inhalers provide ease of use; the medicaments have rapider onset of time resulting from local administration and they have fewer side effects. Various inhalers have been designed in order to provide effective and sufficient delivery of the medicaments used in the treatment of respiratory diseases, particularly in asthma and chronic obstructive pulmonary disease. These inhalers vary according to their operating mechanisms and the physical form of the medicament to be delivered.

In the inhalers used to deliver the medicaments in dry powder form, the medicament is carried in reservoirs, capsules or blisters packages. It is highly significant to deliver each dose to the patient with exact accuracy and preciseness since the required medicament dose in the inhalation is very low.

In general, one blister pocket containing medicament in dry powder form is opened in response to each actuation of the device in inhalers comprising blister packages. One blister pocket containing one dose of dry powder medicament is usually opened by peeling the blister package indexed upon the actuation of the device or piercing the blister pocket by the piercing means in the inhaler. The inhalers comprising peelable blister packs enable the sufficient amount of the dry powder medicament contained in the opened blister to be easily inhaled as the airflow enters the opened blister pocket more easily in the inhalers comprising peelable blister packs than the inhalers comprising pierceable blister packs. Therefore, the blister package should be indexed enough to enable the blister pocket to be opened completely so as to realize an effective inhalation in response to each actuation of the inhaler. However, it is quite difficult to enable the blister package to be indexed properly to the same extent in each actuation of the device so as to realize a safe inhalation in the inhaler comprising peelable blister packages. In the case that the blister package that is indexed upon the actuation of the device is indexed less than the required extent, the blister pocket may not be opened completely while more than one blister pocket may be opened in the case that the blister package is indexed more than the required extent. The fact that one blister pocket cannot be opened completely and an effective inhalation cannot be realized as the sufficient amount of the active agent comprised in the dry powder medicament cannot be delivered to the patient or more than the required amount of the active agent is delivered to the patient as one blister pockets are opened lead to dangerous consequences. Therefore, controlled dosing of the medicament in dry powder form cannot be achieved when the blister package is not indexed properly to the same extent in response to each actuation of the inhaler.

The inhalation device marketed under the trade mark Diskus® by GlaxoSmithKline is one of the most well-known inhalers on the market. This device operates with a slide mechanism and a blister strip package in which the dry powder medicament is carried. However, this device needs to be improved in terms of specifications to enable the blister package to be properly indexed to the same extent in response to each actuation of the device.

The inventor has surprisingly found that the force of attraction imposed by the winding wheel on the lid sheet is balanced, and thus the blister package is properly indexed to the same extent in response to each actuation of the device in the case that each of the preferably polyoxymethylene resilient wings of the winding wheel, on which the lid sheet of the blister package peeled upon the actuation of the inhaler is coiled, is composed of three parts in the inhaler comprising peelable blister package.

To this respect, the present invention relates to an inhaler comprising peelable blister package appropriate for delivering dry powder medicament which enables the blister package to be indexed properly to the same extent in response to each actuation of the inhaler.

DETAILED DESCRIPTION OF THE INVENTION

Figure 1A:
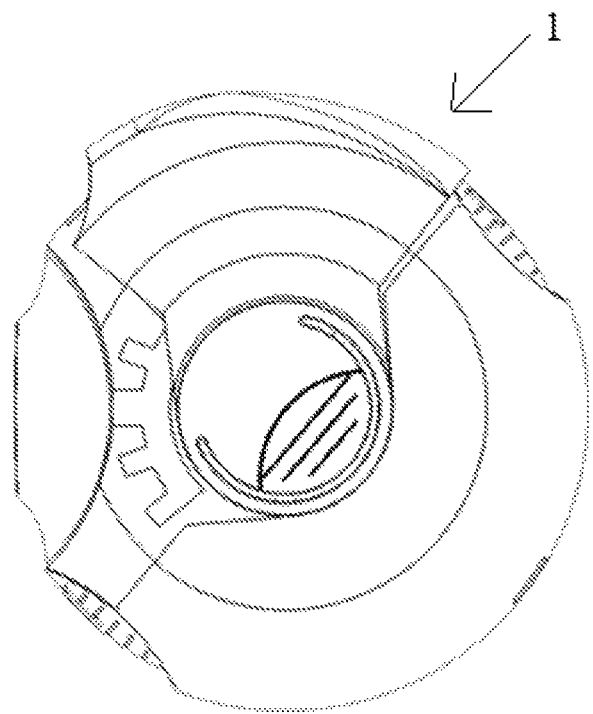
FIG. 1a is a perspective view of the inhaler according to the present invention.
Figure 1B:
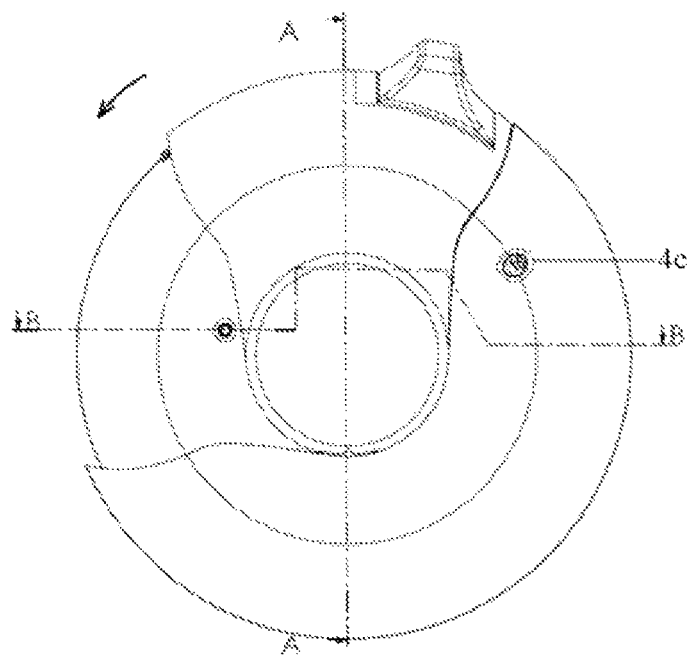
FIG. 1b is another perspective view of the inhaler according to the present invention.
Figure 1C:
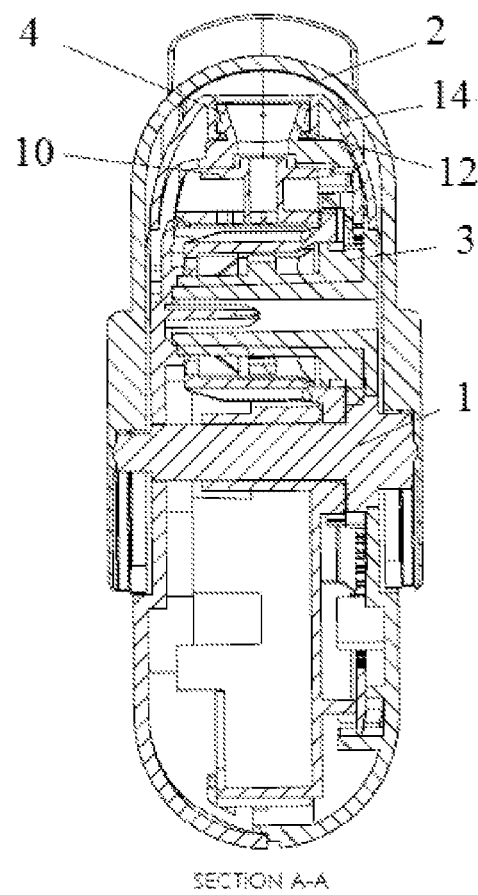
FIGS. 1c and 1d are views of the A-A and B-B cross sections of the inhaler of the present invention, respectively.
Figure 1D:
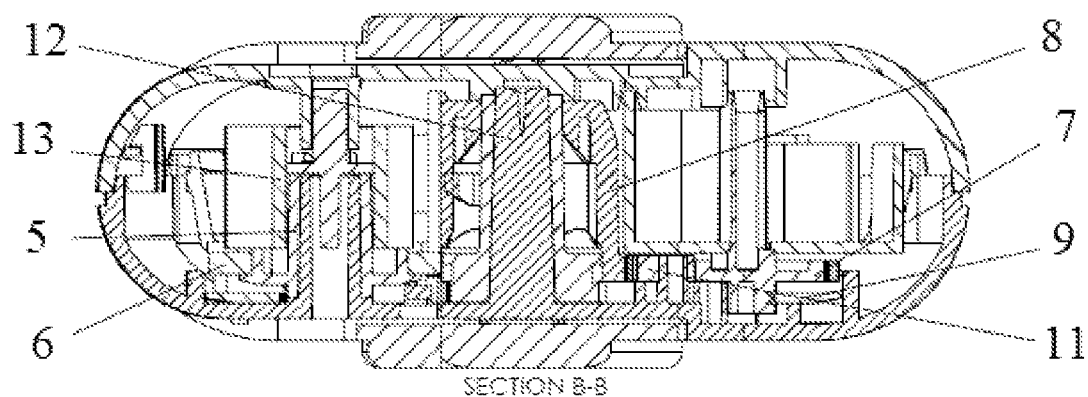
Figure 2A:
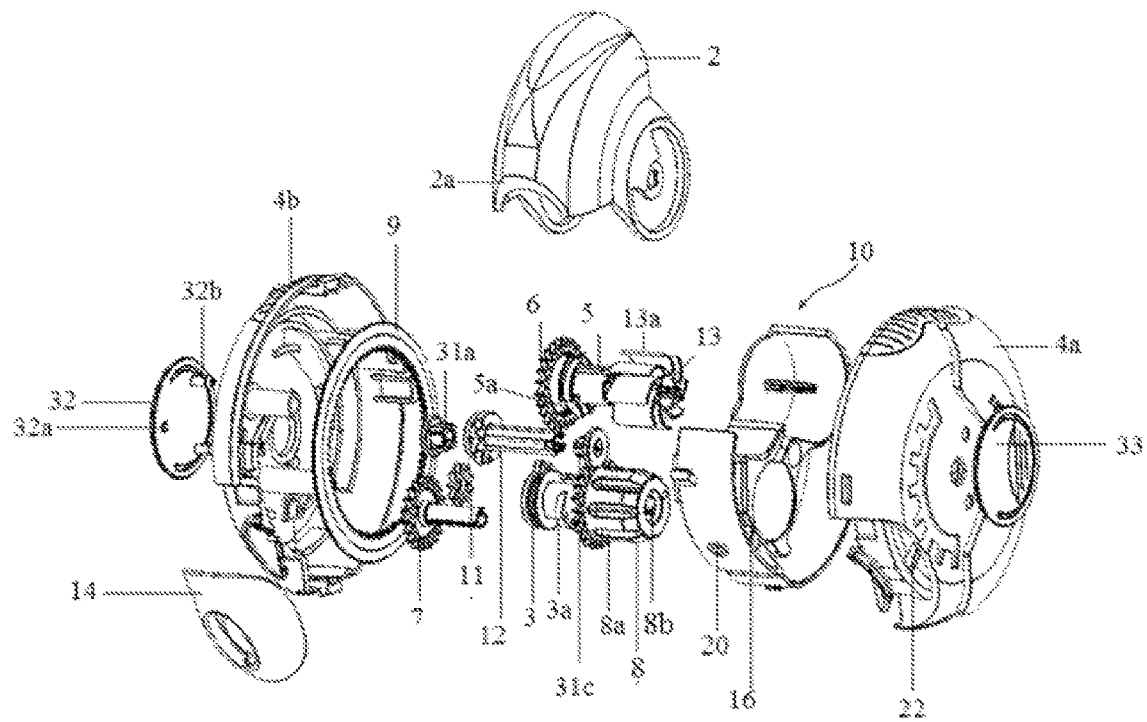
FIG. 2a is an exploded view of the inhaler according to the invention.
Figure 2B:
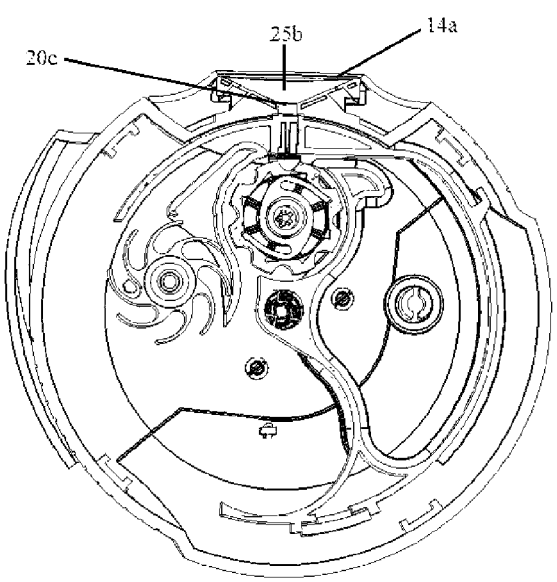
FIG. 2b is a vertical cross-sectional view of the inhaler according to the present invention.

The inhaler (1) pertaining to the present invention comprises a gear mechanism situated in the housing (10) between the upper housing member (4a) and the lower housing member (4b) in order to enable the inhalation of the dry powder medicament carried in a blister package (15) as displayed in FIGS. 1a and 2a. Each component of the inhaler (1) is positioned at suitable spots on the housing (10) to guarantee their working properly and accurately. The cross-sectional view A-A in FIG. 1c and the cross-sectional view B-B of FIG. 1d clearly display the communication of the gear mechanism with the other components of the inhaler (1) and their locations.

The inhaler (1) pertaining to the present invention shown in FIGS. 1a and 2a is ready for inhalation. In this case, the mouthpiece cover (2) is in the second position and the mouthpiece (14) is entirely exposed. The mouthpiece cover (2) has to be rotated by holding on the carved part (2a) on one end of the mouthpiece cover (2) in order to switch to the second position from the first position wherein the mouthpiece is completely covered. In this way, the mouthpiece (14) is completely exposed when the mouthpiece cover (2) is switched to the second position from the first position and the gear mechanism is triggered by the drive gear (12). The drive gear (12) precisely transmits the movement of the mouthpiece cover (2) to the indexing ratchet wheel (3).

Figure 3:
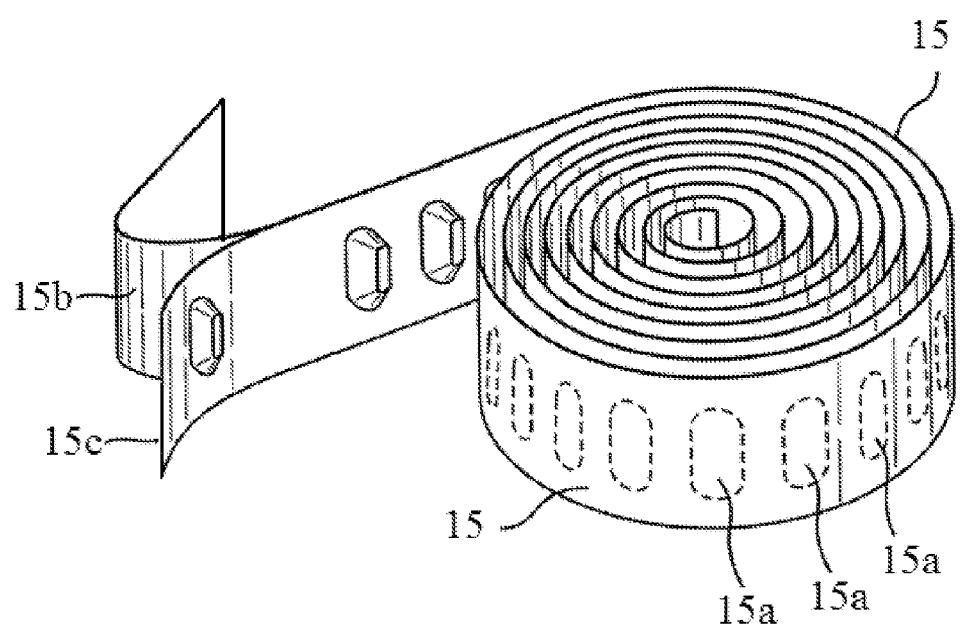
FIG. 3 is a perspective view of the blister pack for use with the inhaler according to the invention.

The indexing wheel (8) which engages with the indexing ratchet wheel (3) enables the blister package (15) shown in FIG. 3 to be indexed. The blister pockets (15a) composing the blister package are received in the recesses (8a) on the indexing wheel and the blister package (15) is indexed when the indexing wheel (8) rotates. In the inhaler pertaining to the present invention, shapes of the recesses (8a) on the indexing wheel (8) have been designed to match the shapes of the blister pockets (15a) composing the blister package (15) for the blister package to be indexed properly.

The blister package (15) shown in FIG. 3 is composed of the lid sheet (15b) which provides impermeability and the base sheet (15c) on which the blister pockets (15a) are spaced at equal intervals. Each blister pocket contains medicament in dry powder form comprising one or more active agents.

The rotational movement that the mouthpiece cover (2) of the device executes while switching from the first position to the second is transmitted to the indexing ratchet wheel (3) via the drive gear (12) that the mouthpiece cover (2) engages with. As displayed in FIG. 2a, arms (3a) of the indexing ratchet wheel interlocks with protrusions inside the indexing wheel (8) and rotates the indexing wheel (8) unidirectionally. Therefore, the blister package (15) is indexed forward while the indexing wheel (8) rotates as the blister pockets (15a) composing the blister package (15) are received in the recesses (8a) of the indexing wheel. The beak (16) in the housing (10) provides the blister package (15) to be peeled while the blister package (15) is indexed and provides one blister pocket (15a) to be opened in response to each actuation of the inhaler (1).

The winding wheel gear (6), which is another component of the gear mechanism, engages with the indexing wheel (8) as displayed in FIG. 2a. The mechanism gear (5) that interlocks with the winding wheel (13) from inside has arms (5a) to interlock with the interior teeth of the winding wheel gear (6). When the indexing wheel (8) rotates the winding wheel gear (6), the winding wheel rotates unidirectionally owing to the arms of the mechanism gear (5a) which interlocks with the interior teeth of the winding wheel gear (6) and the lid sheet (15b) which is peeled away while the blister package is indexed is tightly coiled on the resilient wings (13a) of the winding wheel. The base sheet (15c) of the blister package (15) where the blister pockets are spaced is accumulated in a separate part (18a) of the device (FIG. 4j). Each resilient wing (13a) of the winding wheel extends from the center of the winding wheel (13) to the end.

Figure 12:
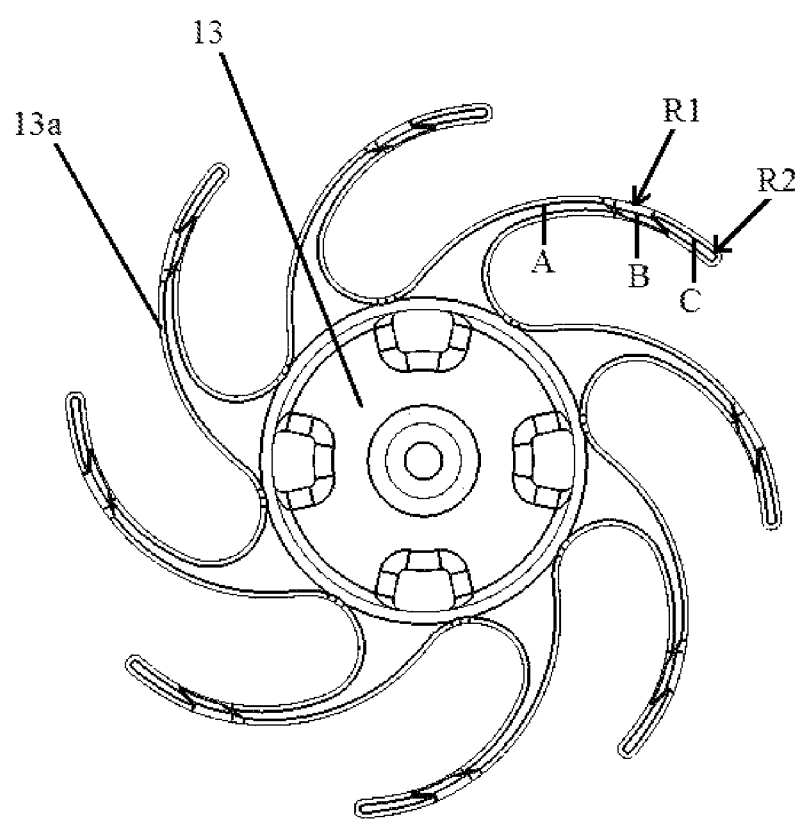
FIG. 12 is a perspective view of the winding wheel pertaining to the present invention.

As illustrated in FIG. 12, the winding wheel (13) of the inhaler pertaining to the present invention is composed of a plurality of resilient wings which are preferably made of polyoxymethylene plastics. Each of these resilient wings (13a) is composed of three parts (A, B, C) each of which has different radius values. Thus, these resilient wings (13a) stretch enough to balance the force of attraction imposed on the lid sheet (15b) of the blister package, therefore on the blister package (15), as the thickness of the lid sheet (15b) of the blister package coiling on them increases, and they enable the blister package (15) to be indexed properly to the same extent in response to each actuation of the inhaler. The resilient wings of the winding wheel illustrated in FIG. 12 are composed of 3 parts (A; B; C). The average radius (R1) of the second part (B) of each resilient wing is in the range of 4.60 mm to 5.20 mm, preferably in the range of 4.75 mm to 5.15 mm; and the radius (R2) of the piece of the third part (C) that curls through the end of the resilient wing is in the range of 0.9 mm to 1.70 mm, preferably in the range of 1.10 mm to 1.50 mm.

The housing of the device of the present invention has been designed such that each component of the blister package and the gear mechanism, which have a significant role in enabling the device to work properly, is situated accurately and works harmoniously. To this end, the housing is divided into several compartments. The used portion and the unused portion of the blister package are accommodated in separated compartments in order to prevent the medicament in dry powder form remaining in the opened blister pocket spilling the other components of the housing. Furthermore, the housing also comprise a beak which enables the blister package to be peeled and a manifold through which the dry powder medicament in the open blister passes before reaching the mouthpiece during inhalation. The housing can be in any appropriate shape, while it is preferably elliptic or circular.

An upper and a lower housing members interlock with each other and enclose the housing in order to keep the housing and the gear mechanism fixed together. The mouthpiece cover hiding the mouthpiece is rotated by being slid on the upper and lower housing members. Carved parts on the surface of the lower and the upper housing members provide effective actuation by preventing the slipping of the finger while rotating the mouthpiece cover. The upper and the lower housing members can be in any appropriate shape which provides ease of use.

The mouthpiece cover hiding the mouthpiece of the device of the present invention has been designed such that it also actuates the device. When the upper and the lower housing members of the device are joined together, engagement tabs on the inside surface of the lower housing member engage with engagement recesses on the inside surface of the upper housing member and the upper and lower housing members are fixed tightly. In addition, the protrusions on the upper and the lower housing members are joined end to end and form a restricted path where the mouthpiece cover rotates. Before each inhalation, both the mouthpiece is uncovered and one dose of the medicament in dry powder form becomes ready for inhalation as one of the blister pockets is opened as a result of the mouthpiece cover being manually rotated along the path restricted by joining the protrusions on the upper and the lower housing members. The rotational path on which the cover moves is restricted on both ends by the protrusions of the upper and the lower housing members. The constant-distance path that the protrusions of the upper and the lower housing members define results in the mouthpiece cover being rotated by a fixed angle in the range of 30° to 160°, preferably, 50° to 120°, most preferably 55°, 60°, 65°, 70°, 75°, 80° to 92.5°, 95°, 97.5°, 100°, 102.5°, 105°, 107.5°, 110°, 112.5°, 115° in response to each actuation of the device.

The mouthpiece cover that triggers the gear mechanism of the device can be found in one of two positions. After pressing the pressing button of the stopper, the mouthpiece cover can easily be switched from the first position to the second position. When the mouthpiece cover is in the first position, the mouthpiece cover resides on the protruding part in one end of the rotational path. When the first position is on, the mouthpiece cover is completely covered and the device is in standby mode. When the mouthpiece cover is in the second position, the mouthpiece cover resides on the protruding part in the other end of the rotational path and one dose of the dry powder medicament becomes ready for inhalation upon the actuation of the device. The mouthpiece cover has two connection points. One of them is on one side of the mouthpiece cover and the other is on another side of the mouthpiece cover to enable the mouthpiece cover to be connected with the inhaler. The mouthpiece cover of the inhaler is joined with the gear mechanism by the drive gear via one connection point of the mouthpiece cover. Only one end of the drive gear is connected with one connection point of the mouthpiece cover while the other end of the drive gear is not connected to the mouthpiece cover at any points. The end of the drive gear that is fixed into one connection point of the mouthpiece cover has a hole at the centre. In addition, each of the connection points itself is a hole in shape. Therefore, the end of the drive gear is passing through the connection point of the mouthpiece cover while the extension part present at the centre of the inside surface of the protective cover is passing through both the centre of said end of the drive gear and the connection point of the mouthpiece cover.

Shape of the one connection point of the mouthpiece cover is different from shape of other connection point of the mouthpiece cover as well as shape of the end of the drive gear that is connected to one connection point of the mouthpiece cover is different from shape of other end of the drive gear.

The shape of the end of the drive gear that matches with the connection point of the mouthpiece cover through which said end of the drive gear passes, has surface area in the range of 30-100 $mm^2$ preferably in the range of 32-90 $mm^2$ and more preferably in the range of 40-80 $mm^2$ and particularly in the range of 45, 46, 47, 48, 49, 50, 51, 52, 53, 54, 55 to 60, 61, 62, 63, 64, 65, 66, 67, 68, 69, 70, 71, 72, 73, 74, 75 mm². Adjustment of the surface area to the range given above enables transmission of the force of at least 5 Newton that is applied to afford the rotational movement of the mouthpiece cover to be transmitted to the gear mechanism accurately. In addition, the shape of the end of the drive gear is preferably quadrangular, most preferably a trapezoid, with a surface area in defined range. Therefore, the one end of the drive gear with the surface area in the range of 30-100 mm² passes through one connection point of the mouthpiece cover and this enables the rotational movement of the mouthpiece cover to be transmitted to the gear mechanism accurately via only one end of the drive gear and enables the mouthpiece cover synchronize with the drive gear.

Figure 4A:
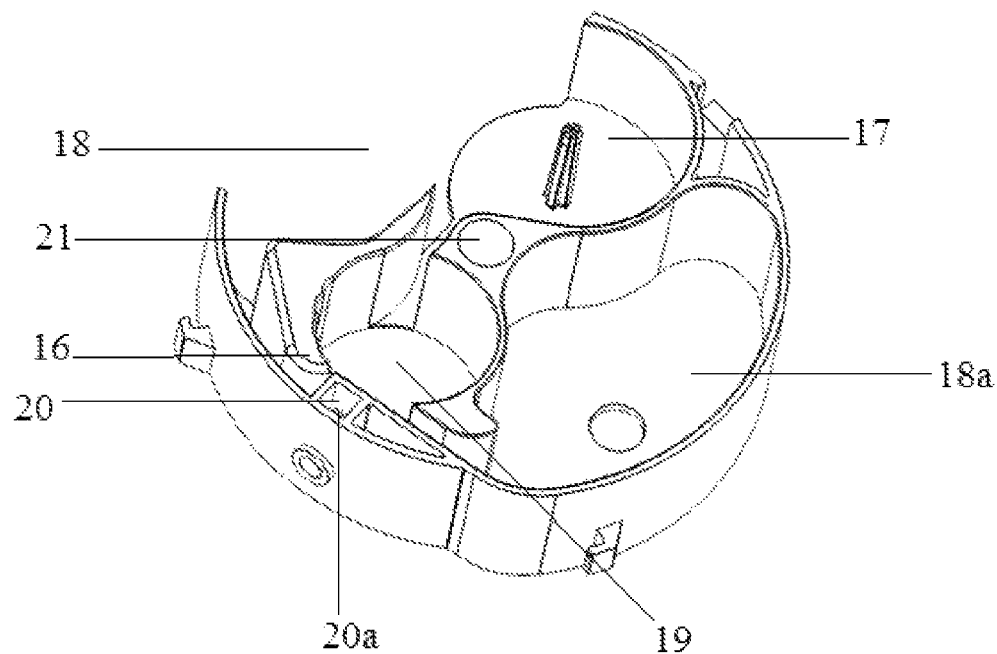
FIGS. 4a and 4b are perspective views of the housing of the inhaler according to the invention.
Figure 4B:
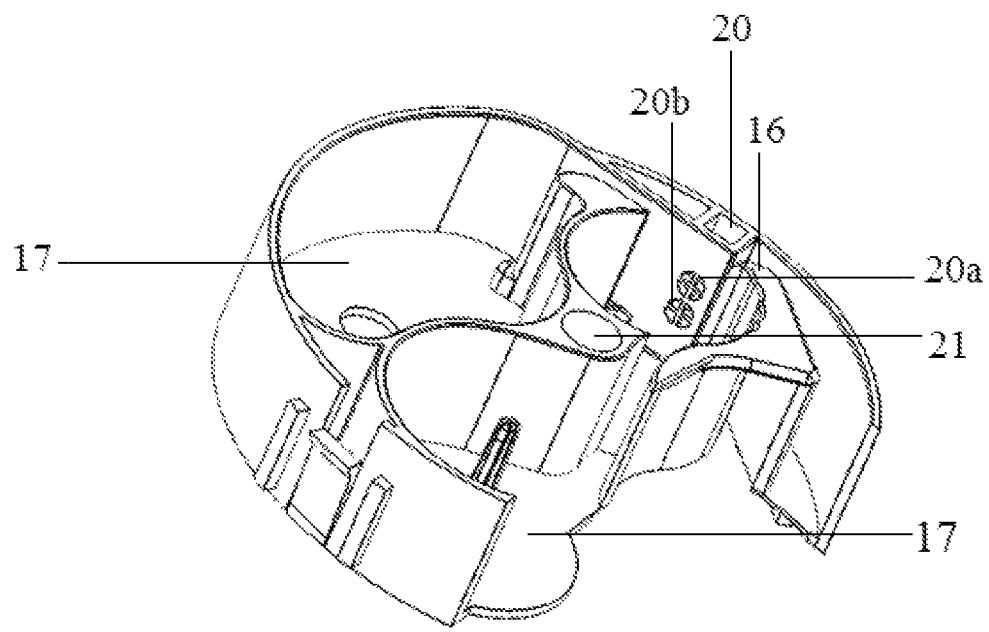

Different views of the housing (10) wherein the gear mechanism and the other components of the inhaler (1) pertaining to the present invention are arranged are displayed in FIGS. 4a and 4b. Furthermore, as can be seen in FIGS. 4a through 4j, the housing (10) also comprises the components having significant roles in the actuation of the device such as the beak (16), the manifold (20), the apertures with four sub-apertures (20a, 20b). Each component comprised in the housing is situated in appropriate parts of the housing (10) in order to enable the inhaler (1) to work properly. The drive gear (12) passes through the center (21) of the housing and joins the mouthpiece cover (2) at both sides of the inhaler. The blister package (15) is in the lower part (17) of the housing as coiled up. In response to each actuation of the inhaler (1), the blister package (15) is peeled by the beak (16) in the housing while being indexed by the indexing wheel (8) situated in the upper part (19) of the housing. The lid sheet (15b) of the blister package (15) which provides impermeability is indexed over the beak (16) and coiled on the winding wheel (13) which is situated in the side part (18) of the housing. The base sheet (15c) of the blister package (15) on which the blister pockets (15a) are spaced, on the other hand, is accumulated in the separated compartment (18a) of the housing (10). Upon the inhalation of the patient, the air passes through the air inlet with four sub-apertures (20a) under the manifold (20) into the opened blister pocket; entrains the dry powder medicament contained in the opened blister pocket (15a) in response to each actuation of the device; provides it to pass through the other aperture with four-sub-apertures (20b) and reach the mouthpiece via the manifold (20).

In each actuation of the inhalation device, the gear mechanism is triggered by the rotation movement of said mouthpiece cover from the first position to the second position along the rotational path restricted on both ends by the protrusion parts on the upper and the lower housing members to provide the blister package to be advanced. In each actuation of the device, the constant-distance path that the protrusions of the upper and the lower housing members define allows said mouthpiece cover to be rotated by a fixed angle. Accordingly, because of the fact that the one end of the drive gear that matches with the connection point of the mouthpiece cover through which said end passes is in a shape that has a surface area in the range of 30-100 mm², in each actuation of the inhalation device, only rotation of said mouthpiece cover from the first position to the second position on the constant-distance path guarantees that the blister package is advanced by the same distance and the opened blister is at accurate position so that the sufficient amount of the dry powder formulation contained in the opened blister can be inhaled. In addition to this, the patient is sure about whether the blister is opened completely or not by controlling the position of the mouthpiece cover on the constant-distance path. In other words, if the mouthpiece cover is in the second position wherein it resides on the protrusion part on the other end of the constant-distance rotational path, the patient is sure about that one blister is completely opened and one dose of the dry powder medicament contained in the opened blister becomes ready for inhalation; if the mouthpiece cover is between the first position and the second position, the patient is sure about that one blister is not completely opened.

According to the present invention, each gear of the gear mechanism in the device directly or indirectly engages with each other. The drive gear, which is one of the components of the gear mechanism, provides the mouthpiece cover to trigger the gear mechanism. In each actuation of the device, the constant-angle rotational movement of the cover is transmitted to gear of an indexing ratchet wheel which interlocks with an indexing wheel via the drive gear. The indexing wheel synchronizes with the indexing ratchet wheel when the mouthpiece cover is switched from the first position to the second position. The gear of the indexing wheel is engaged with a winding wheel gear and a pinion gear and the rotation of the indexing wheel gear causes them to move as well. A mechanism wheel engages with the inside of the winding wheel gear via the arms of the mechanism wheel. A counter gear that engages with a small gear under a base gear rotates by means of the base gear that engages with a pinion gear and a counter gear with movement of the mouthpiece cover. Therefore, with the rotation of the indexing wheel, both the lid sheet of the blister package is provided to be coiled on the wings of the winding wheel as the winding wheel is rotated by the mechanism wheel and the counter gear rotates to display the new number of unused blister from the display aperture.

According to the present invention, the indexing wheel may be another component of the gear mechanism. The recesses of the indexing wheel match with the shape of the blister package. The fact that the blister pockets of the blister package are received in these recesses in sequence while the indexing wheel rotates allows the blister package to be indexed properly. The rotation angle of the indexing wheel depends on the number of the recesses of the indexing wheel. In each actuation of the inhalation device, the indexing wheel can be rotated by the angle of 15° to 120°. According to the invention, there are preferably 8 recesses of the indexing wheel. Therefore, the indexing wheel is supposed to rotate by the angle of 45° in response to each actuation of the device for the opened blister pocket to be positioned accurately. The drive gear which is connected with the mouthpiece cover accurately transmits the constant rotational movement, by an angle in the range of 30° to 160°, preferably, 50° to 120°, most preferably 55°, 60°, 65°, 70°, 75°, 80° to 92.5°, 95°, 97.5°, 100°, 102.5°, 105°, 107.5°, 110°, 112.5°, 115°, of the mouthpiece cover to the gear of the indexing ratchet wheel when the device is actuated. As the arms of the indexing ratchet wheel interlock with the indexing wheel from the inside, the indexing wheel and the indexing ratchet wheel synchronize. Therefore, the constant-angle rotation that the mouthpiece cover executes when the device is actuated causes the indexing wheel to rotate by a constant angle of 45°. The length of the path that the mouthpiece cover follows and the constant angle value is adjusted such that the indexing wheel rotates by 45° in response to each actuation of the device. Thus, the blister package is completely opened for the inhalation of the sufficient amounts of the medicament in dry powder form as a result of the accurate positioning of the blister package in response to each actuation of the device of the present invention. The inhaler of the present invention has a stopper that is situated between the lower housing member and the housing as engaging with the two holes on the lower housing member. This stopper consists of a pressing button, a pawl and a supporting part. Each of the pressing button and the pawl passes through one hole of the lower housing member and is shown from the outside as the supporting part is situated at the inside of the inhaler and is not shown from the outside. According to the present invention, for actuation of the inhaler, the mouthpiece cover is switched from the first position to the second position over the rotational path. However, the pawl is engaged to the recess part on inside surface of the mouthpiece cover to prevent the movement of the mouthpiece cover when the mouthpiece cover is in the first position in which the mouthpiece is completely covered. Since the pressing button moves synchronously with the pawl, when the pressing button is pressed, the pawl is advanced forward inside of the inhaler and disengaged from the mouthpiece cover. After the pawl is disengaged from the mouthpiece cover, the mouthpiece cover can be rotated from the first position to the second position to actuate the inhaler.

Because of the supporting part of the stopper, there is no need for a spring to enable the pressing button to be pressed. There is an end that is integrated with the supporting part and leans the housing of the inhaler. When the pressing button is pressed, the supporting part springs over the end of said supporting part and both of the pressing button and the pawl are advanced forward inside of the inhaler.

Additionally, at least one component which is situated in the lower housing member and serves as another stopper engages with the teeth of at least one of the gears of the gear mechanism and stabilizes the gear in a suitable position in order to prevent backward rotation of the blister package. While the stopper can hinder the rotation of any gear of the gear mechanism, it preferably hinders the rotation of the indexing wheel connected with the indexing ratchet wheel. The stopper can be anywhere suitable in the lower housing member and have any shape. Consequently, the inhaler according to the present invention has two stopper that provide the blister package to be accurately and precisely positioned in response to each actuation of the device as preventing the accidental actuation of the inhaler. Thus, controlled dosing of the dry powder medicament in the opened blister pocket is enabled when the device is actuated.

The term "controlled dosing" refers to the intake of the medicament in dry powder form on the required amount.

The housing (10) and the other components of the inhaler (1) pertaining to the present invention are stably kept together as the upper housing member (4a) and the lower housing member (4b) displayed in FIGS. 5a through 5h are joined together. The engagement tabs (28) on the inside surface of the lower housing member (4b) engage with the engagement recesses (27) on the inside surface of the upper housing member (4a) and the upper and lower housing members are fixed tightly. Therefore, the protrusions (23a, 23b) on the upper housing member (4a) and the protrusions (24a, 24b) on the lower housing member (4b) are joined end to end and they define the restricted path for the rotational movement of the mouthpiece cover (2). The mouthpiece cover (2) can be moved along this path. When the mouthpiece cover (2) is on the first position, the mouthpiece is completely covered, the device is in standby mode and the mouthpiece cover (2) leans on the first protrusion (23a) on the upper housing member and the first protrusion (24a) on the lower housing member. The mouthpiece (14) is manually slid along the rotational path with the help of the carved part to switch to the second position. The mouthpiece is completely exposed when the cover is in this position, one dose of the dry powder medicament is ready for inhalation and the mouthpiece cover (2) leans on the second protrusion (23b) on the upper housing member and the second protrusion (24b) on the lower housing member.

Figure 4C:
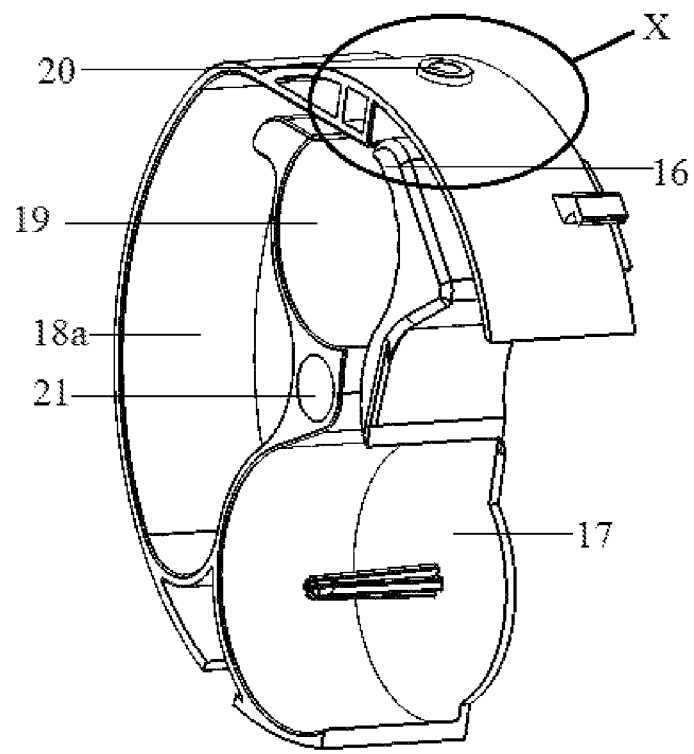
FIG. 4c is another perspective view of the housing of the inhaler according to the invention.
Figure 4D:
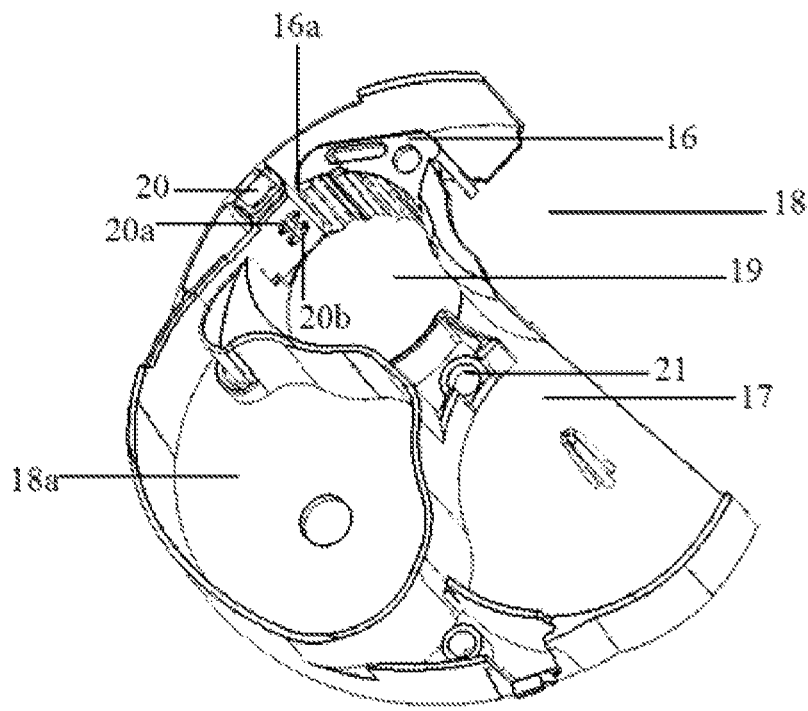
FIG. 4d is another perspective view of the housing of the inhaler of the invention.
Figure 4E:
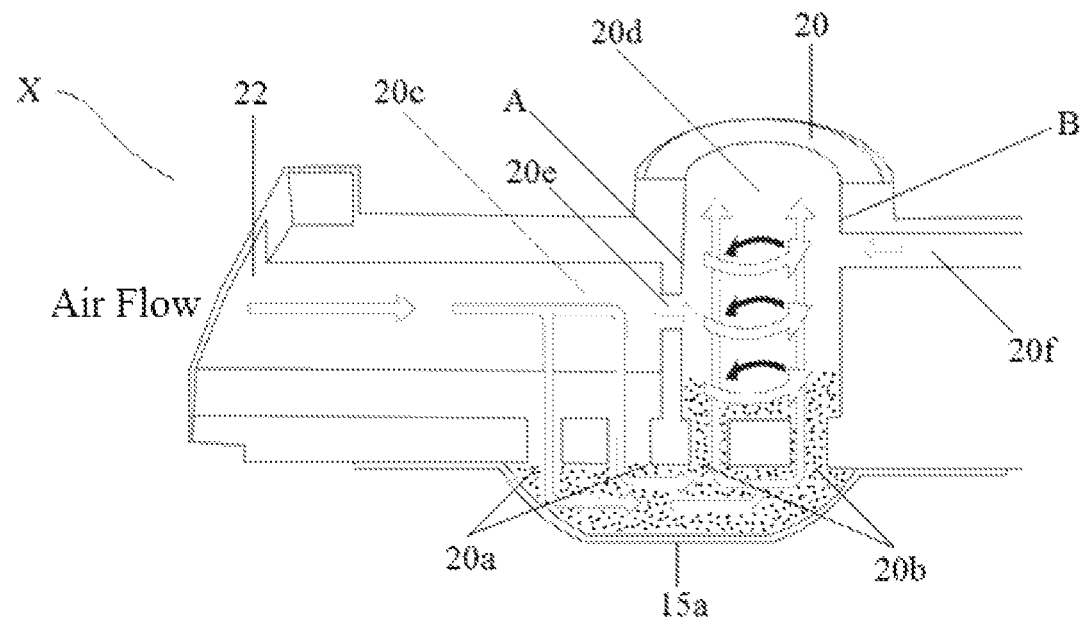
FIGS. 4e and 4f are cross-sectional views of the manifold part of the inhaler pertaining to the invention which is shown as X in FIG. 4c.
Figure 4F:
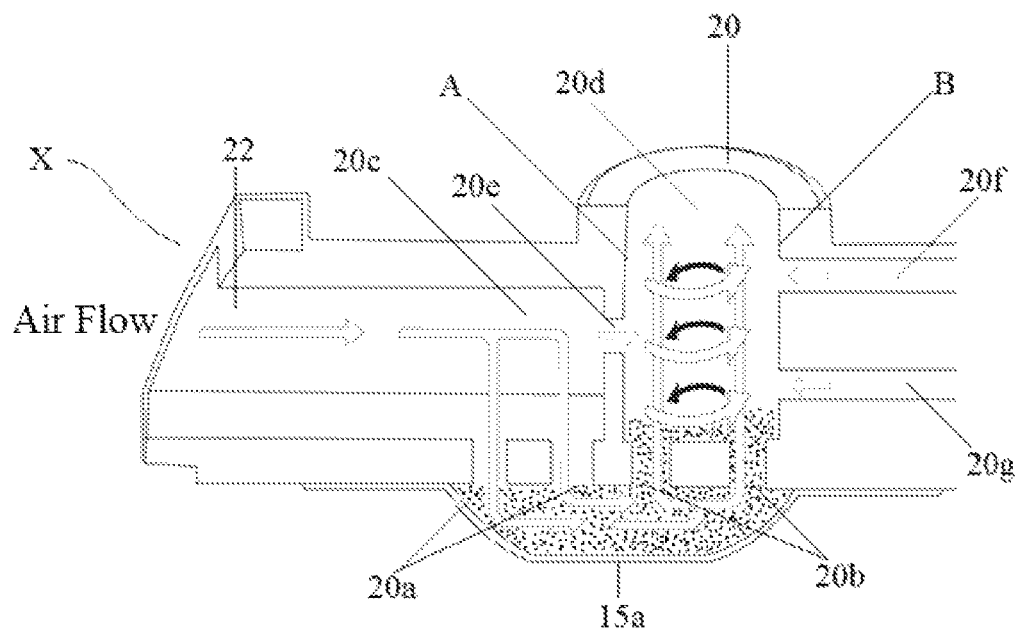
Figure 4G:
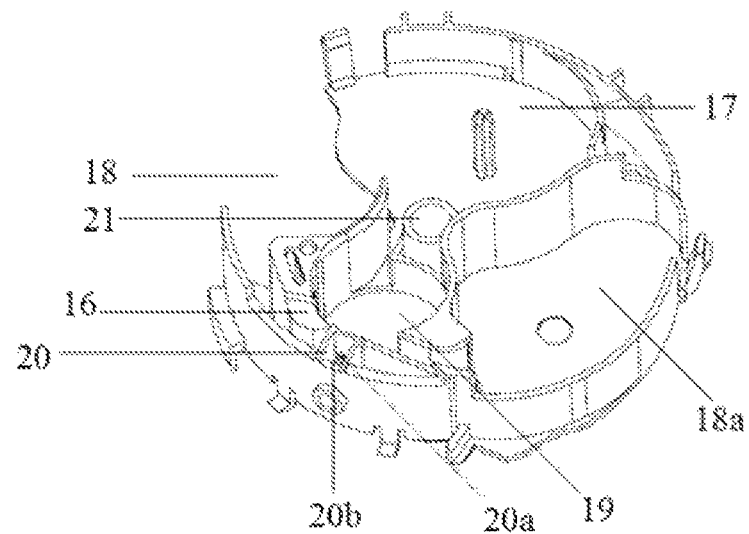
FIGS. 4g and 4h are perspective plan and bottom views of the housing of the inhaler according to the invention, respectively.
Figure 4H:
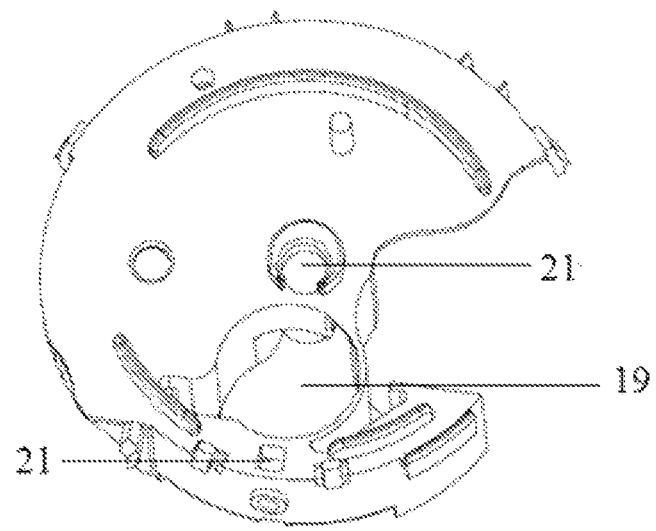

A view of the cross-section of the housing (10) which illustrated as X in FIG. 4c and includes the manifold (20) is given in FIGS. 4e and 4f. According to FIG. 4e, the blister pocket (15a) opened upon the actuation of the inhaler (1) is positioned immediately under the apertures with four sub-apertures (20a, 20b). There are two apertures with four sub-apertures (20a, 20b) on the edge of the manifold (20) which is close to the blister (15a) and they are partitioned off from each other by a wall. This wall is named as wall A in FIG. 4c and it partitions the manifold (20) into two parts. Wall A lies between the first part (20c) and the second part (20d) of the manifold and it belongs to both the first part (20c) and the second part (20d) of the manifold. Upon the respiration of the patient so as to inhale the medicament in dry powder form in the opened blister pocket (15a), the external air that enters the inhaler passing through the air inlet (22) on the upper housing member reaches the first part (20c) of the manifold. Some part of this airflow reaches the opened blister (15a) by passing through the aperture with four sub-apertures (20a) on the edge of the first part of the manifold. The airflow reaching the opened blister pocket (15a) entrains the dry powder medicament in the blister to the second part (20d) of the manifold through the other aperture with four sub-apertures (20b) on the edge of the manifold which is close to the blister. Wall A and wall B shown in FIG. 4c are two opposite walls in the second part (20d) of the manifold. Some part of the external air which runs through the air inlet (22) and enters the inhaler (1) upon the patient's breathing in passes through the first part (20c) of the manifold and reaches the opened blister pocket (15a) while the rest passes through the aperture (20e) on wall A and the aperture (20f) on wall B and enters the second part (20d) of the manifold. The apertures (20e, 20f) on wall A and wall B are asymmetrically positioned. Shapes and the cross-sections of the apertures (20e, 20f) on wall A and wall B can be identical or different. Thus, an effective turbulence is created in the second part (20d) of the manifold as the speed of the airflow entering through the aperture (20e) on wall A and the speed of the airflow entering through the aperture (20f) on wall B are different. The created turbulence disperse the agglomeration of the dry powder medicament entrained to the second part (20d) of the manifold and provides the dry powder medicament to be delivered to the patient at appropriate particle size distribution.

Another cross-sectional view of the part of the housing which is shown as X in FIG. 4c is given in FIG. 4f. In the cross-sectional view of the manifold illustrated in FIG. 4f, there are two apertures (20f, 20g) on wall B of the manifold differently from FIG. 4e. The apertures (20e, 20f) on wall A and wall B are asymmetrically positioned with respect to each other. The shapes and the cross-sections of the apertures (20e, 20f, 200 on wall A and wall B which allow the air in the second part (20d) of the manifold can be identical or different. Thus, the airflow entering in through the aperture (20e) on wall A and the airflows entering in through the apertures (20f, 20g) on wall B create an effective turbulence in the second part (20d) of the manifold. This turbulence disperses the agglomeration in the dry powder medicament entrained to the second part (20d) of the manifold and enables the medicament in dry powder form to be delivered to the patient at an appropriate particle size distribution.

The drive gear (12) passes through the aperture (4d) in the center of the upper housing member displayed in FIGS. 5e and 5*f* and the aperture (4*e*) in the center of the lower housing member, then it is joined with the mouthpiece cover (2) on two ends. There is a tapered channel between the manifold (20) and the mouthpiece (14). As displayed in FIGS. 5*c* and 5*d*, one half (25*a*) of the tapered channel that interconnects the manifold (20) that exist in the housing (10) with the mouthpiece (14) is comprised in the upper housing member (4*a*) while the other half of it (25*b*) is comprised in the lower housing member (4*b*). The channel is constituted as a whole when the upper (4*a*) and the lower (4*b*) housing members are joined together. Upon the inhalation of the patient, the air that enters the device through the air inlet (22) arranged in the upper housing member (4*a*) passes through the aperture with four sub-apertures (20*a*), reaches the opened blister (15*a*) and entrains the dry powder medicament there to the manifold (20) by passing it through the other aperture with four sub-apertures (20*b*). The grids on the upper housing member (23*e*, 23*f*) and the grids on the lower housing member (24*e*, 24*f*) prevent the slips of fingers when rotating the mouthpiece cover.

Figure 6A:
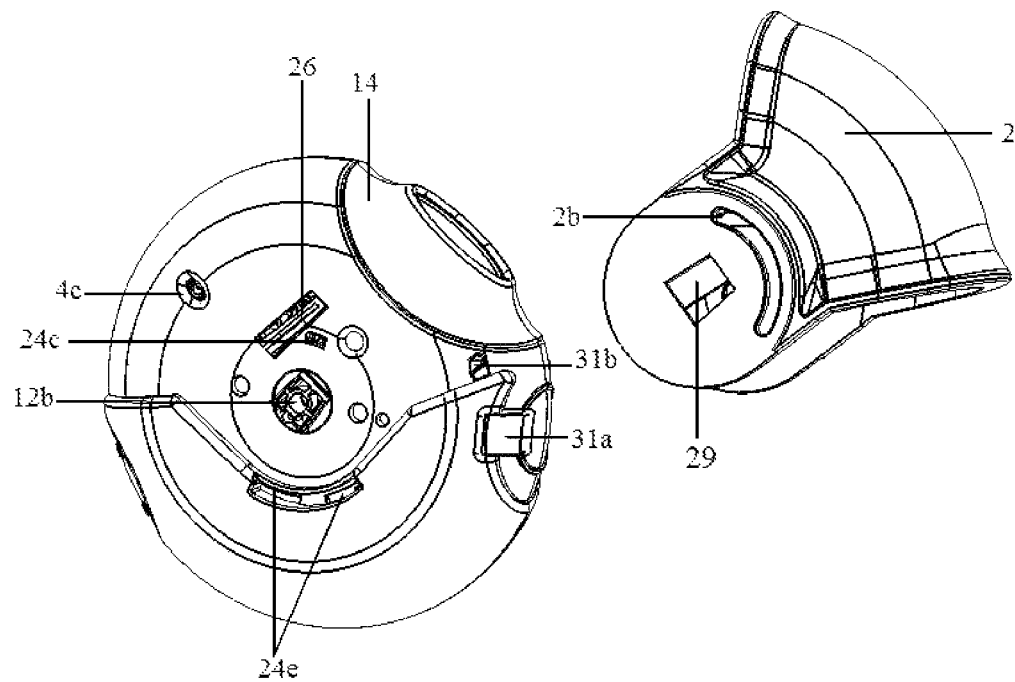
FIG. 6a is a view of the mouthpiece cover exploded from the inhaler.
Figure 6B:
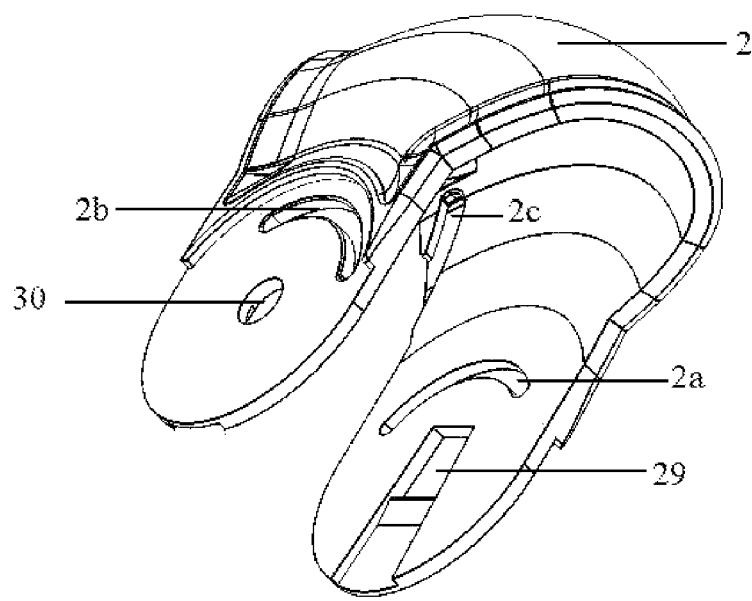
FIG. 6b is another perspective view of the mouthpiece cover of the inhaler of the invention.
Figure 6C:
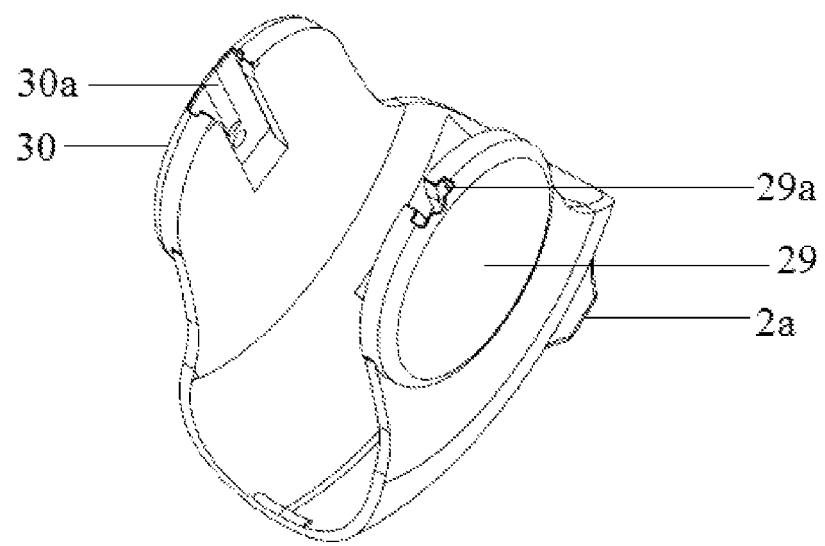
FIGS. 6c and 6d are perspective views of the inner and outer sides of the mouthpiece cover of the inhaler according to the invention, respectively.
Figure 6D:
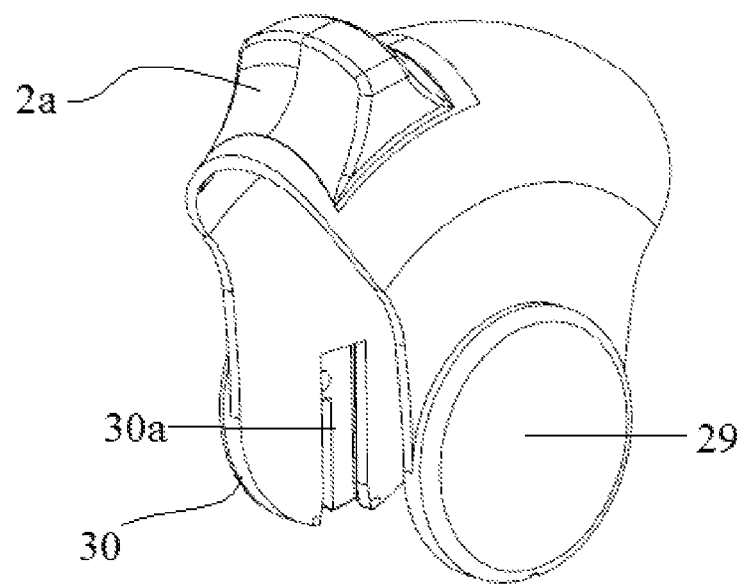
Figure 6E:
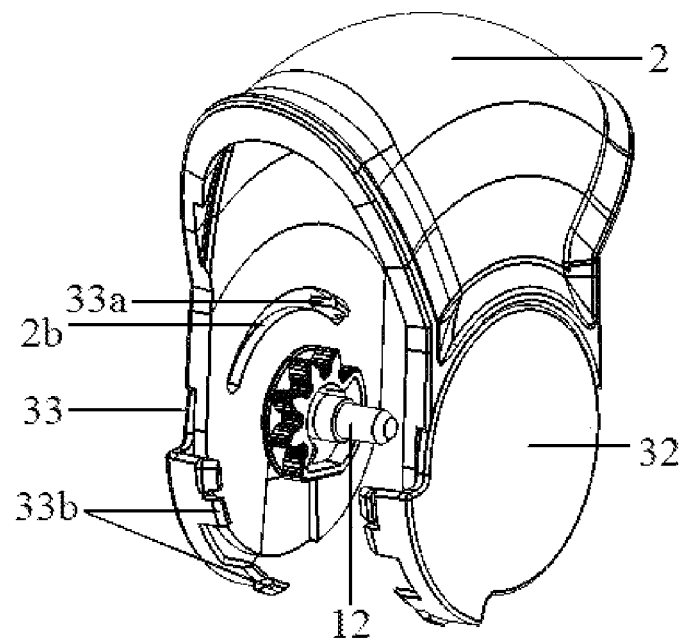
FIG. 6e is a perspective view of the connection between the mouthpiece cover, the drive gear, and the protective covers of the inhaler of the invention.
Figure 6F:
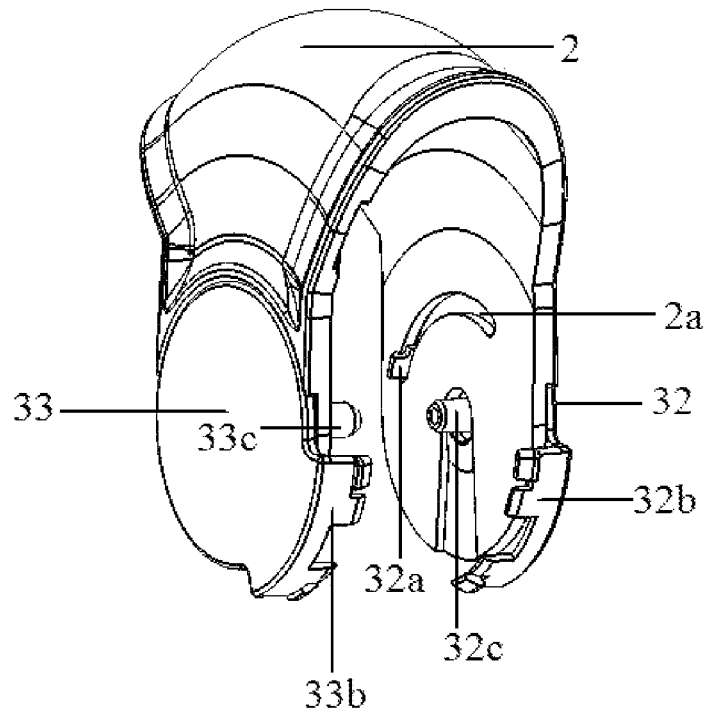
FIG. 6f is a perspective of the connection between the mouthpiece cover and the protective covers of the inhaler of the present invention.
Figure 6G:
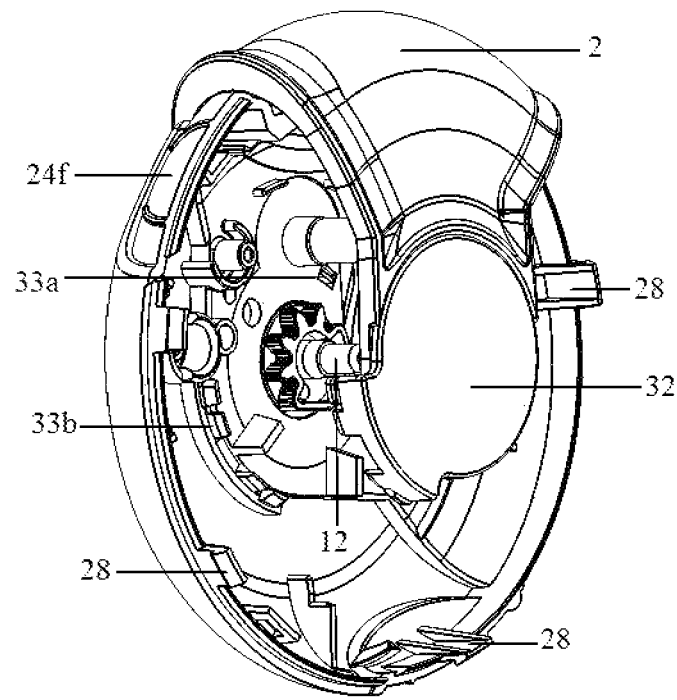
FIG. 6g is a perspective view of the connection between the mouthpiece cover, the drive gear, the lower housing member, and the protective cover of the inhaler of the present invention.
Figure 6H:
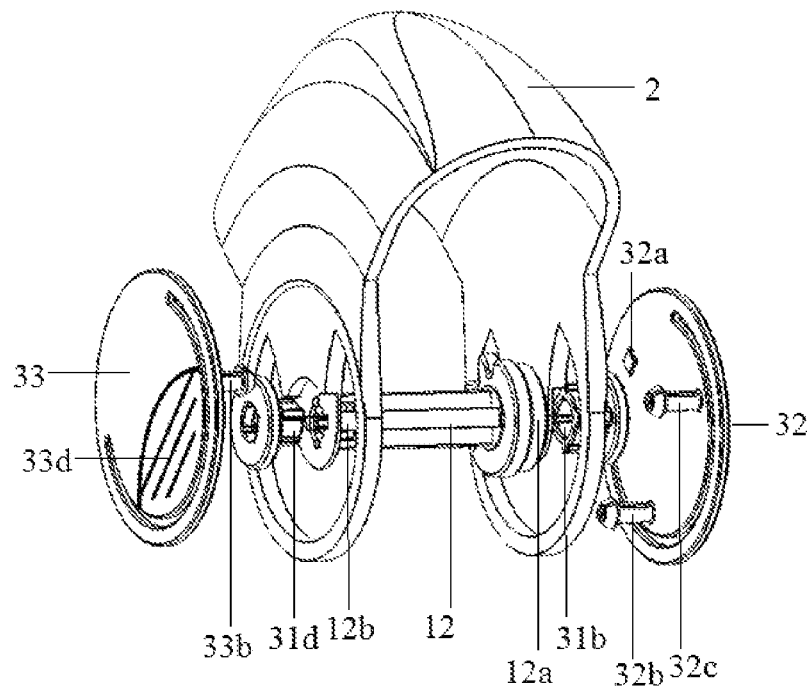
FIG. 6h is an exploded view of the communication between the mouthpiece cover, the drive gear and the stabilizing resilient covers in the inhaler according to the invention.

The mouthpiece cover (2) of the inhaler pertaining to the present invention is displayed in FIGS. 6*a* through 6*f*. The carved part, which is the finger tab (2*a*) in one end of the device enables the mouthpiece cover to be easily removed manually as seen in FIG. 6*d*. The finger tab (2*a*) has been designed to match the finger shape and is situated in any suitable spot on the mouthpiece cover (2). As can be seen clearly in FIGS. 6*c* and 6*d*, the first and the second connection points (29, 30) of the mouthpiece cover have recesses (29*a*, 30*a*) on their inside surfaces. Protrusions (31*a*, 31*b*) on the two ends of the drive gear (12) displayed in FIGS. 7*e* and 7*f* make a male-female connection with these recesses (29*a*, 30*a*). The first recess (30*a*) on the inside surface of the mouthpiece cover engages with the first protrusion (31*a*) on the one end of drive gear while the second recess on the inside surface of the mouthpiece cover (29*a*) engages with the second protrusion (31*b*) on the other end of the drive gear and the connection provided between each end of the drive gear (31*a*, 31*b*) and the corresponding recess (30*a*, 29*a*) on the inside surface of the mouthpiece cover is a male-female connection. The male-female connection that each end of the drive gear (31*a*, 31*b*) makes with the corresponding recessed parts on the inside surface of the mouthpiece cover (30*a*, 29*a*) causes to form an inside lock connection between the drive gear (12) and the mouthpiece cover (2) with maximum ±0.01% margin of error. Therefore, the rotational movement of the mouthpiece cover (2) on the upper (4*a*) and lower (4*b*) housing members is accurately transmitted to the indexing ratchet wheel by the drive gear (12) which has an inside lock connection with the mouthpiece (14) on its two ends.

The mouthpiece cover (2) is joined with the gear mechanism via the connection points. The drive gear consists of two ends (12*a*, 12*b*) and a hole (12*c*) at the center of one end as seen in FIG. 7*g*. Further, the drive gear (12) is joined with the connection points (29, 30) of the mouthpiece cover via the side covers (31*a*, 31*c*) as it can clearly be seen in FIGS. 6*e*, 6*h*, 6*i* and 6*j* illustrating the communication between the mouthpiece cover (2), the drive gear (12), side covers (31*a*, 31*c*) and the stabilizing resilient covers (32,33). Each of these side covers (31*a*, 31*c*) passes through the center (4*d*) of the upper housing member or the center (4*e*) of the lower housing member and joins with the end (12*a*, 12*b*) of the drive gear. It can clearly be seen in FIG. 6*j* that the both ends (12*a*; 12*b*) of the drive gear are carved such that the end of the side cover (31*b*, 31*d*) can pass through. The end of the drive gear (12*a*) that is fixed into one connection point (29) of the mouthpiece cover has a hole (12*c*) at the center. In addition, each of the connection points (29, 30) itself is a hole in shape (FIG. 6*b*). Therefore, the end of the drive gear (12*a*) is fixed into the connection point (29) of the mouthpiece cover while the extension part (33*c*) present at the centre of the inside surface of the protective cover is fixed into both the hole (12*c*) at the centre of said end of the drive gear and the connection point of the mouthpiece cover.

Figure 7A:
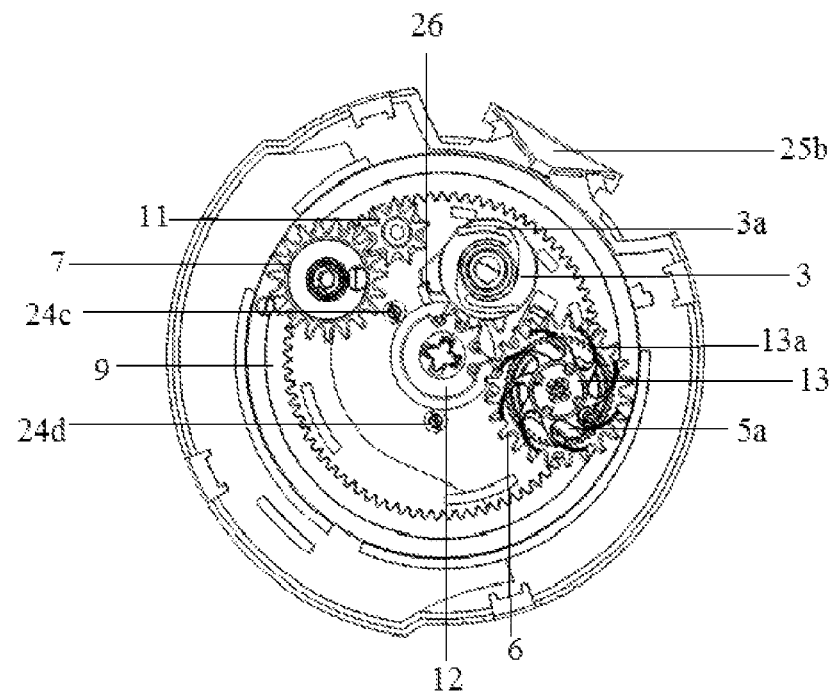
FIGS. 7a and 7b are cross-sectional views of the engagement of the gears composing the gear mechanism with each other in the inhaler according to the present invention.
Figure 7B:
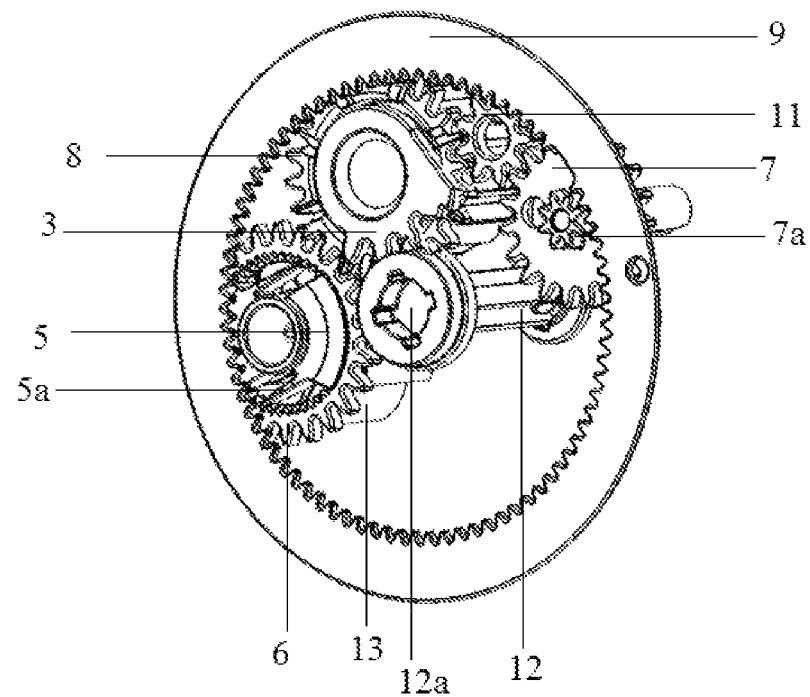
Figure 7C:
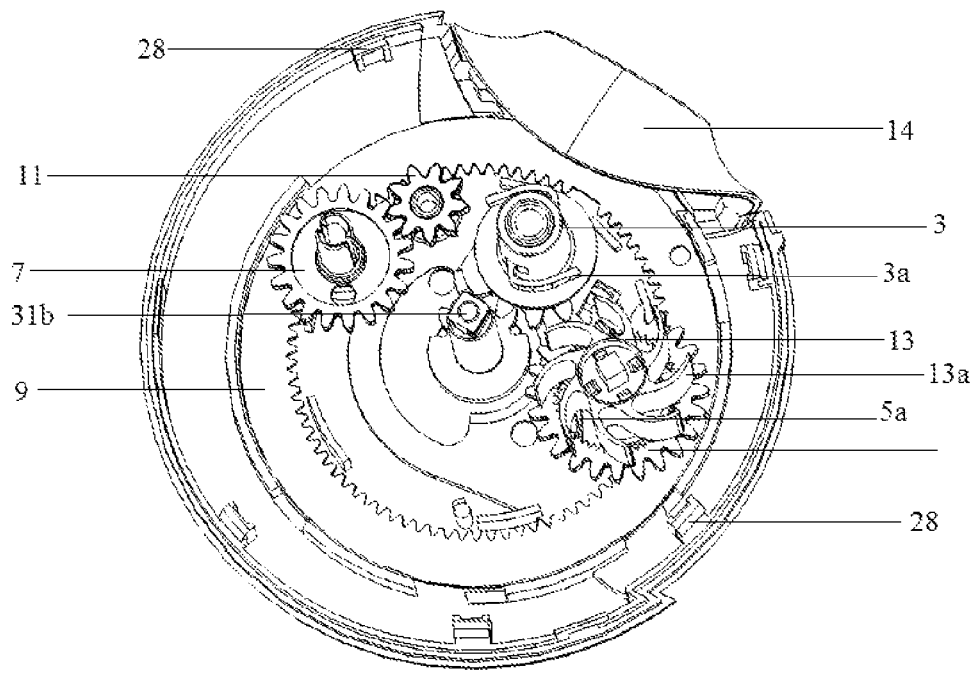
FIG. 7c is a cross-sectional view of the engagement of the gears composing the gear mechanism in the inhaler of the present invention.
Figure 7D:
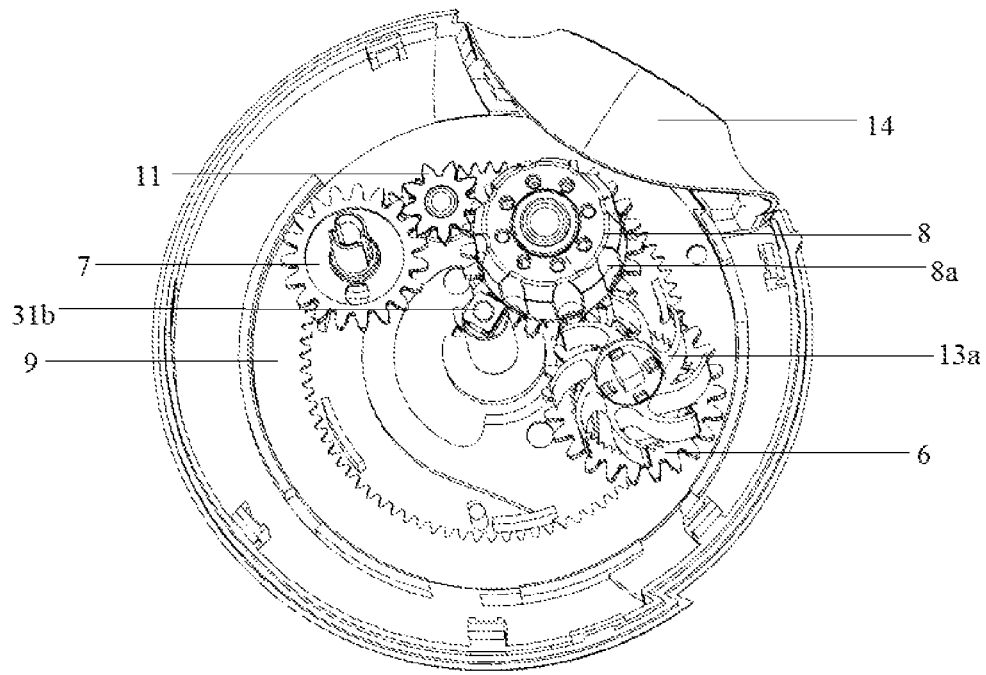
FIG. 7d is another cross-sectional view of the engagement of the gears composing the gear mechanism in the inhaler of the present invention.
Figure 7E:
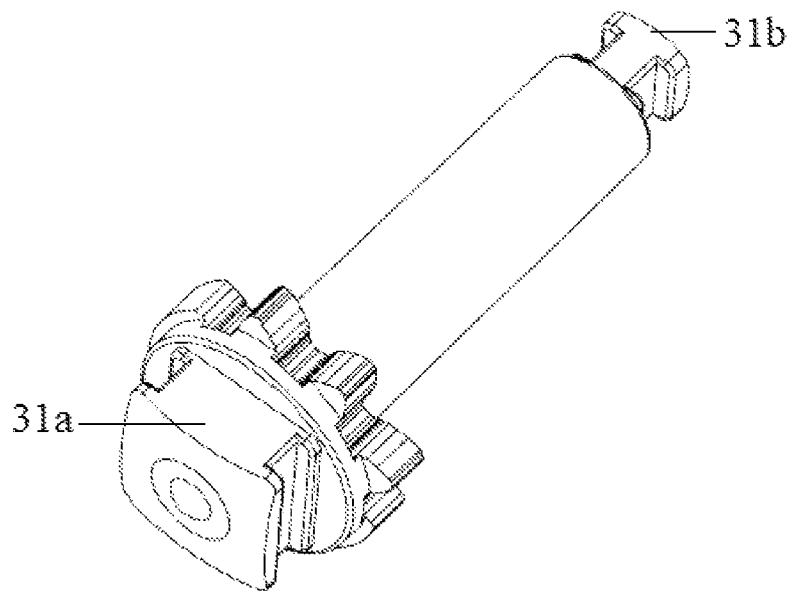
FIGS. 7e and 7f are perspective views of the drive gear of the inhaler according to the invention.
Figure 7F:
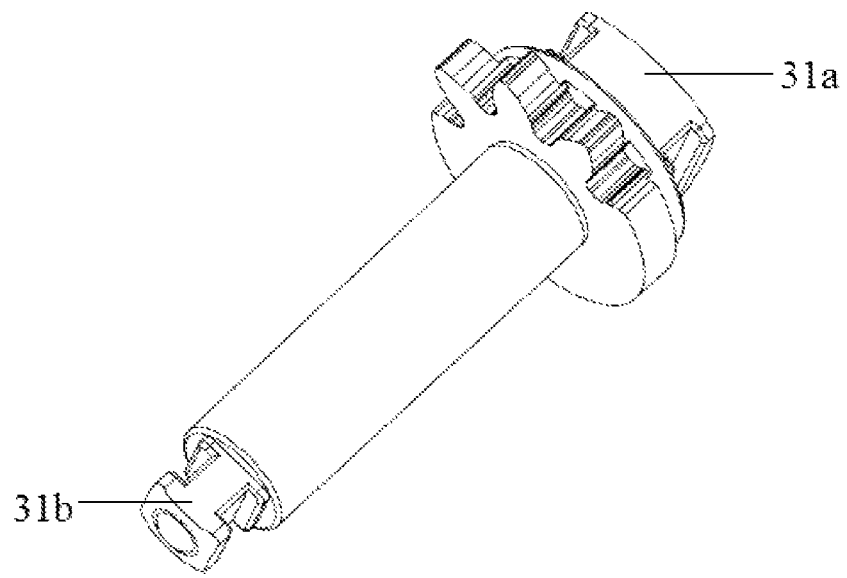

The shape of one connection point (29) of the mouthpiece cover is different from the shape of the second connection point (30) of the mouthpiece cover as well as the shape of the end of the drive gear (12*a*) that is connected with one connection point (29) of the mouthpiece cover is different from shape of other end of the drive gear (12*b*) (FIGS. 6*b*, 7*f* and 7*g*).

Each end of the side covers (31*d*, 31*b*) passes through one of the connection points (29, 30) of the mouthpiece cover and it is received in the recess in one end (12*b*, 12*a*) of the drive gear, thus it provides to tightly and stably interconnect the mouthpiece cover (2) with the drive gear (12). It is provided that the mouthpiece cover (2) synchronizes with the drive gear (12) as the connection point (29, 30) of the mouthpiece cover which has a matching shape with the ends (31*d*, 31*b*) of the side covers that passes through it on both sides of the device and the end (12*b*, 12*d*) of the drive gear that it communicates with are on the same component.

As is seen from FIGS. 6*a* through 6*j*, and 7*h*, the shapes of the ends (31*b*; 31*d*) of the side covers that are received in the carved parts on the ends of the drive gear and the shapes of the connection points (29, 30) of the mouthpiece cover are not identical since the two ends (12*a*, 12*b*) of the drive gear are not identical.

The mouthpiece cover (2) rotates by the same angle each time it is switched from the first position to the second position on the path restricted by the protrusions (29*a*, 29*b*, 30*a*, 30*b*) on the upper and the lower housing members (4*a*, 4*b*). The rotational angle of the mouthpiece cover (2) varies depending on the shape and the size of the device but is a fixed value between 30° and 160°. This angle is adjusted according to the shape and the size of the device such that the indexing wheel (8) having 8 recesses (8*a*) rotates 45 degrees in response to each actuation of the device. The mouthpiece cover (2) rotates by the same angle on its two ends in response to each actuation of the device and this rotational movement of the mouthpiece cover (2) is accurately transmitted to the indexing wheel (8) by the indexing ratchet wheel (3) because of the drive gear (12) which is tightly attached to the mouthpiece cover (2) and the indexing wheel is provided to rotate 45° each time the device is triggered.

Figure 2C:
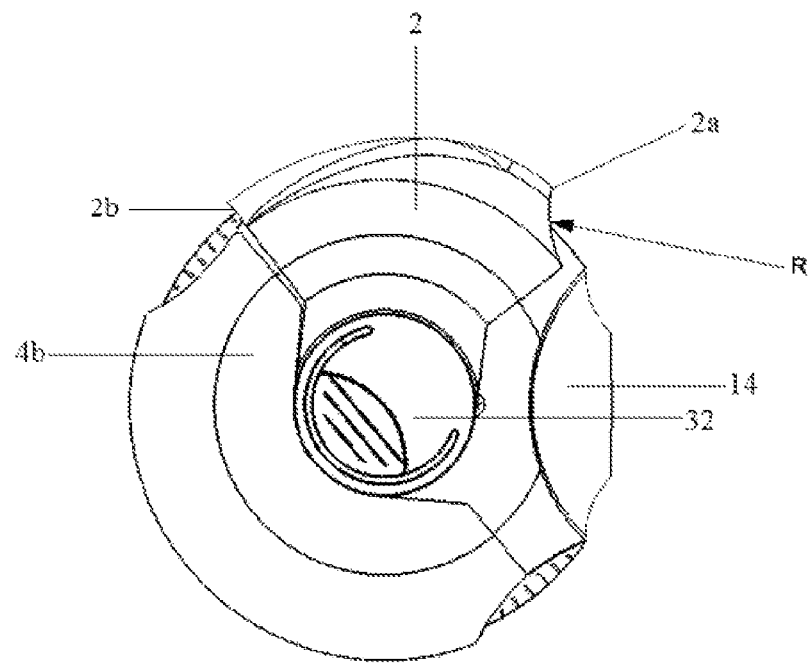
FIG. 2c is a front view of the inhaler according to the present invention.

The mouthpiece cover (2) can be rotated by holding from the front end (2*a*) or back end (2*b*) of it with the help of the thumb. Therefore, the front end (2*a*) or the back end (2*b*) of the mouthpiece cover (2) is in contact with the patient's finger while it is moved manually. According to FIG. 2*c*, only the front end (2*a*) of the mouthpiece cover (2) of the inhaler is carved such that it matches with the shape of the thumb so as to provide the mouthpiece cover (2) to be rotated easily and rapidly while the back end (2*b*) of the mouthpiece cover is not carved. However, it is probable that both the front end (2*a*) and the back end (2*b*) of the mouthpiece cover are carved. The shape of the carved part in the front end (2*a*) of the mouthpiece cover resembles to the shape of the thumb for the thumb to be placed in this carved part exactly in order to rotate the mouthpiece cover. Thus, the carved part of the front end (2*a*) of the mouthpiece cover illustrated in FIG. 2*c* is in the shape of the arc of the circle which has a radius (R) in the range of 30 mm to 40 mm, preferably in the range of 32.5 mm to 37.5 mm. In more detail, the carved part (2a) in the front end of the mouthpiece of the device shown in FIG. 2c is in the shape of the arc of 45° of said circle.

Figure 2D:
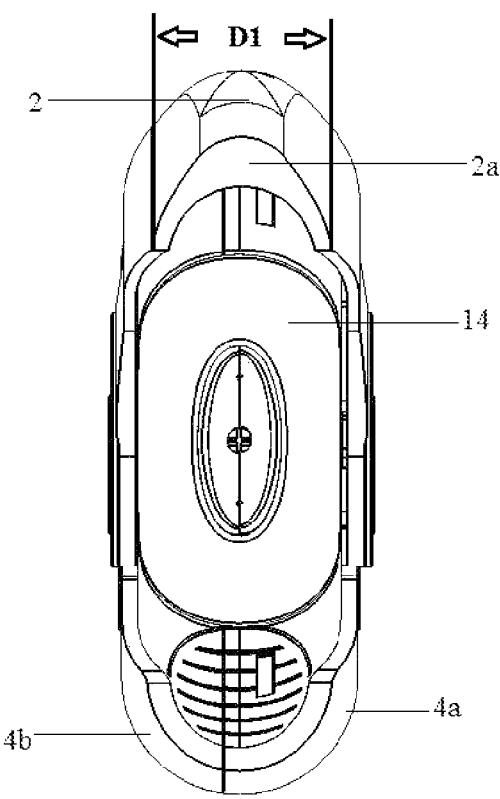
FIG. 2d is a lateral view of the inhaler according to the present invention.

In addition, another variable contributing to the carved part in the front end (2a) of the mouthpiece cover to match with the shape of the thumb is the width of the mouthpiece cover (2) illustrated as D1 in FIG. 2d. For the thumb to be able to grip the cover and impose force, a particular part has to be in contact with the carved part in the front end (2a) and the back end (2b) of the mouthpiece cover. To this end, D1 distance is in the range of 10 mm to 20 mm, preferably in the range of 11 mm to 16 mm.

Figure 8:
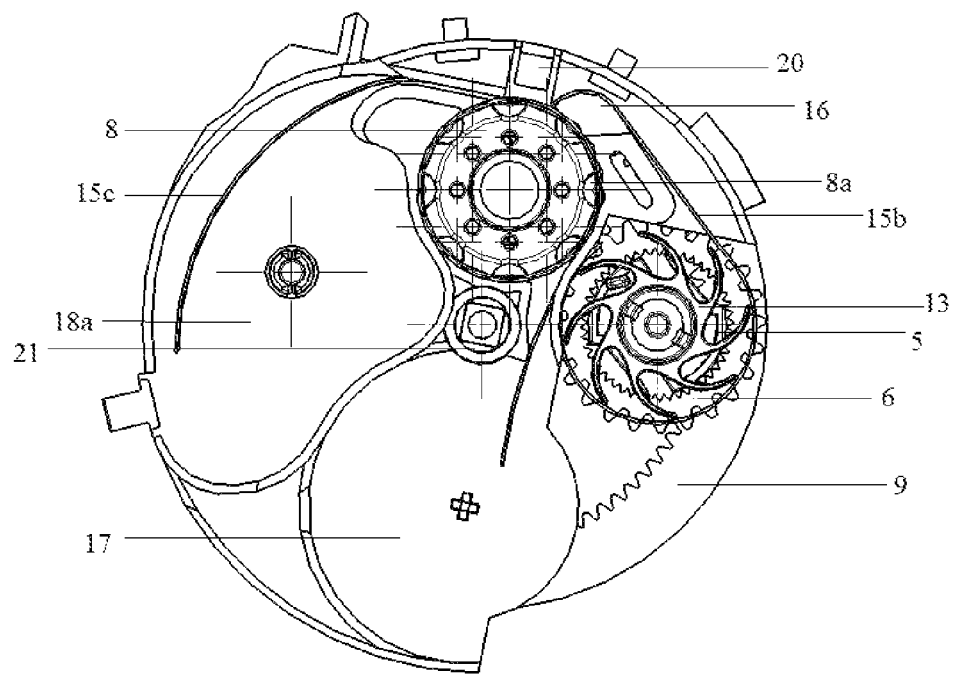
FIG. 8 is a cross-sectional view of the blister package delaminating in course of operation of the inhaler according to the present invention.

There are 8 recesses (8a) on the indexing wheel displayed in FIG. 2a and the indexing wheel (8) rotates 45° each time for the blisters received in these recesses to be able to be positioned accurately. The blister package (15) is indexed by the 45° rotation of the indexing wheel (8) in response to each actuation of the device and is peeled by the beak (16) so one dose of the dry powder medicament becomes ready for inhalation when one blister pocket is opened. As seen in FIG. 8, the lid sheet (15b) that is peeled away by the beak (16) and the base sheet (15c) of the blister package (15) are enclosed in separate compartments. The lid sheet (15b), which provides impermeability of the blister package, passes over the beak (16) and tightly coils on the wings (13a) of the winding wheel. The base sheet (15c) with blister pockets (15a), each of which comprises one dose of the dry powder medicament, is accumulated in the separated compartment (18a) in the housing (10). In response to each actuation of the inhaler (1), one dose of the dry powder medicament becomes ready for inhalation after one blister pocket (15a) is opened; the air which enters the device through the air inlet (22) upon the inhalation of the patient entrains the dry powder medicament to the mouthpiece and provides to deliver it to the patient.

Figure 6I:
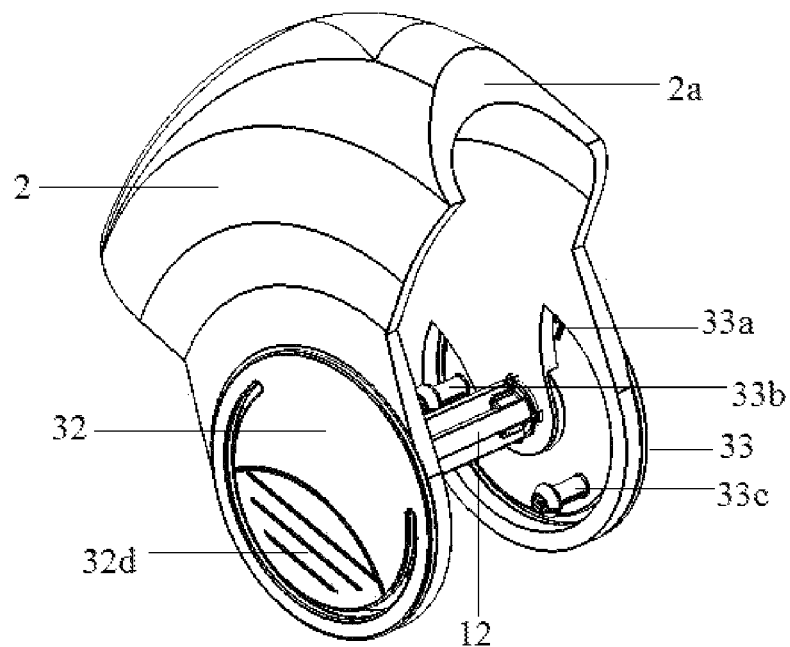
FIG. 6i is a cross-sectional view of the communication between the mouthpiece cover, the drive gear and the stabilizing resilient covers in the inhaler according to the invention.
Figure 6J:
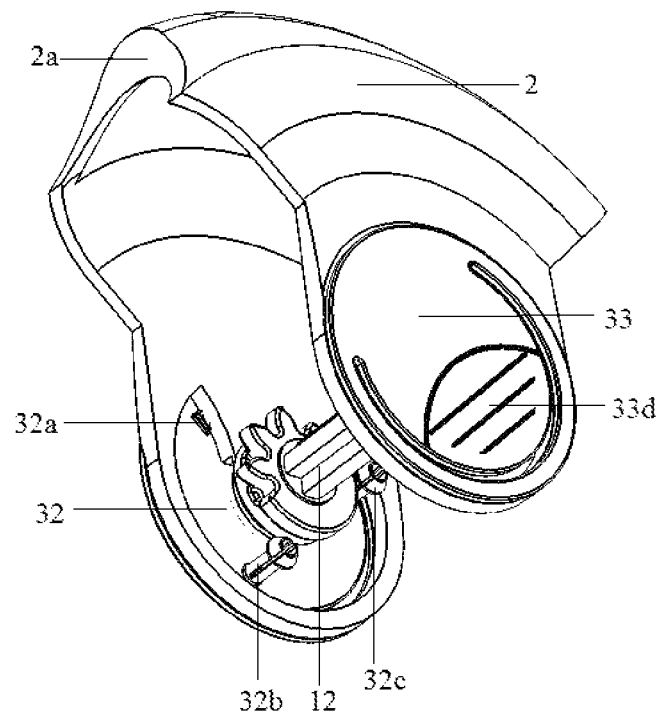
FIG. 6j is a cross-sectional view of the communication between the mouthpiece cover, the drive gear and the stabilizing resilient covers in the inhaler according to the invention.
Figure 7G:
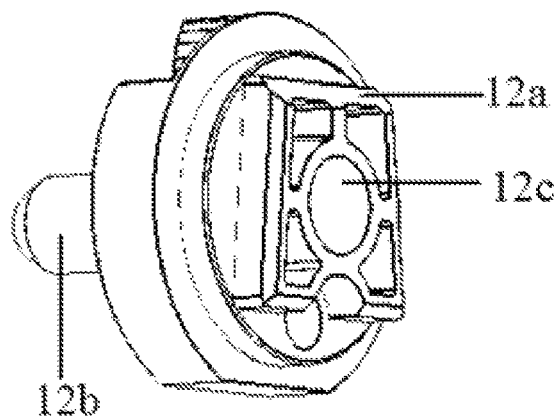
FIG. 7g is a perspective view of the drive gear of the inhaler of the invention.
Figure 7H:
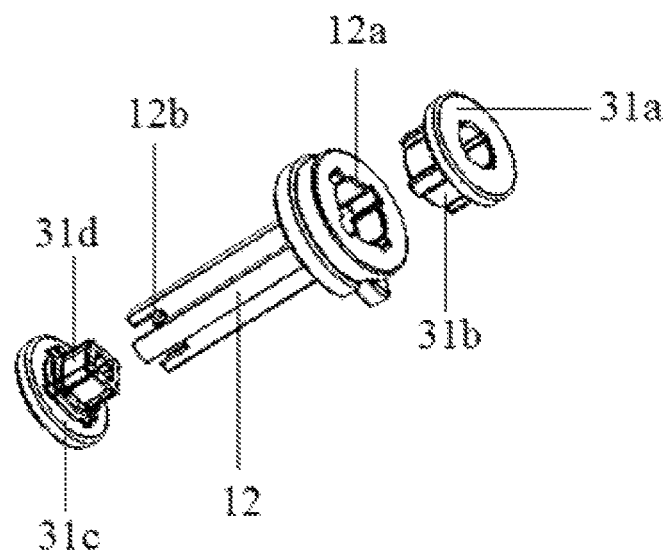
FIG. 7h is an exploded view of the communication between the drive gear and the side covers in the inhaler according to the invention.

There is one stabilizing resilient cover (33; 32) on each connection point (29; 30) of the mouthpiece and on each side cover (31c; 31a), as displayed in FIGS. 2a, 6a, 6h-6j and 5i. When the mouthpiece cover (2) is in the first position, the pawls (32a, 33a) under the stabilizing resilient covers, which are on the connection points (29, 30) of the mouthpiece, interlock with the mouthpiece cover (2) on both sides as clearly seen in FIGS. 6i and 6j. The pawl (33a) under the stabilizing resilient cover that is on the first connection point (29) interlocks with the mouthpiece cover on one side (FIG. 6i). Identically, the pawl (32a) under the stabilizing resilient cover that is on the second connection point (30) of the mouthpiece cover interlocks with the mouthpiece cover (2) on the other side (FIG. 6j). Thus, these pawls (32a, 33a) under the stabilizing resilient covers prevent the movement of the mouthpiece cover (2) by interlocking with it on both sides.

Figure 5A:
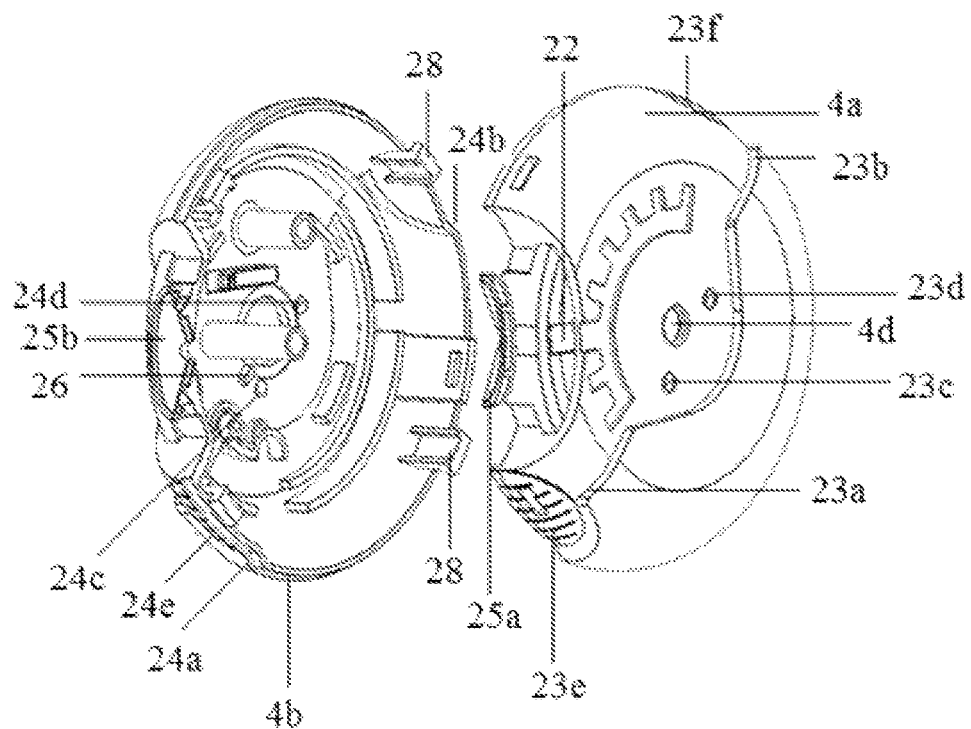
FIGS. 5a and 5b are perspective views of upper and lower housing members of the inhaler according to the invention, respectively.
Figure 5B:
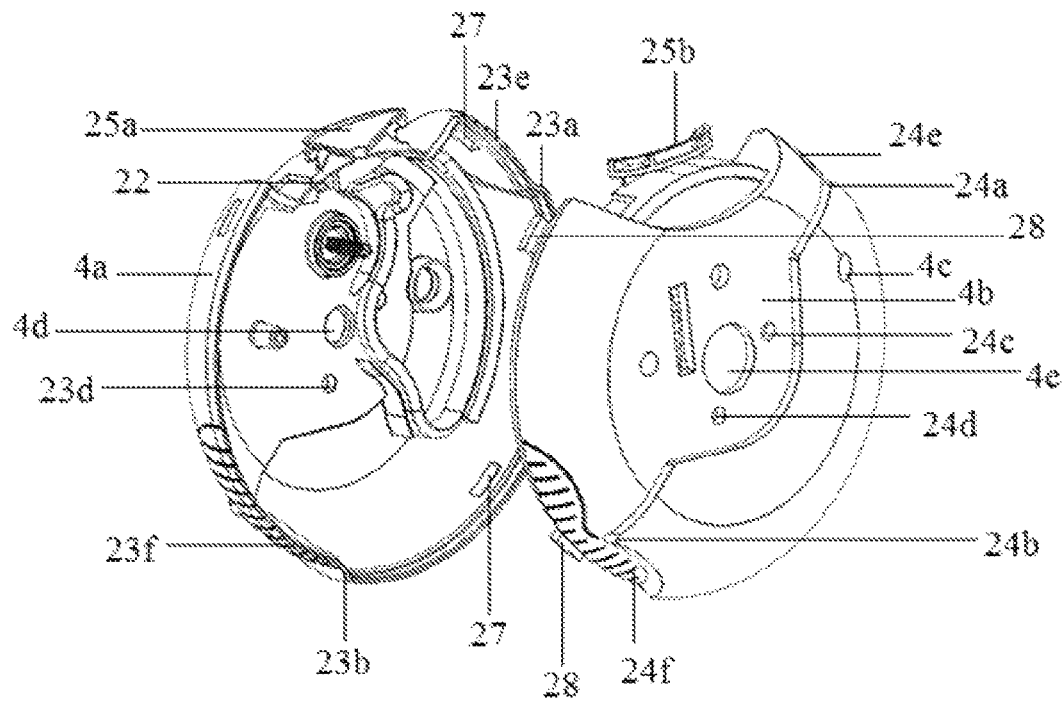
Figure 5C:
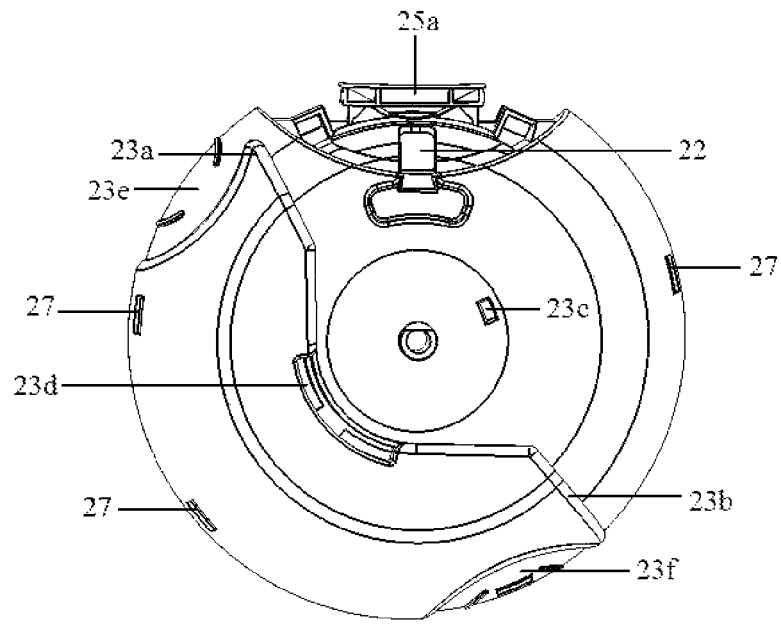
FIG. 5c is another perspective view of the upper housing member of the inhaler of the invention.

The extensions (32b, 32c, 33b, 33c) under the stabilizing resilient covers pass through the apertures (23c, 23d, 24c, 24d) on the upper and the lower housing members illustrated in FIGS. 5a and 5b and provide the stabilizing resilient covers to remain stable. Namely, the extensions (33b, 33c) under the stabilizing resilient cover that is on the first connection point (29) of the mouthpiece cover pass through the apertures (23c, 23d) on the upper housing member and provide one of the stabilizing resilient covers (33) to be stably joined with the device. Identically, the extensions (32b, 32c) under the stabilizing resilient cover on the second connection point (30) of the mouthpiece cover pass through the apertures (24c, 24d) on the lower housing member and provide one of the stabilizing resilient covers (32) to be stably joined with the device as clearly illustrated in FIG. 5i.

Before the inhalation, the resilient parts (32d, 33d) of each stabilizing resilient cover illustrated in FIGS. 6i and 6j are pressed on for raising the pawls (32a, 33a) and releasing the mouthpiece cover (2) in order to actuate the gear mechanism of the device to prepare one dose of dry powder medicament before inhalation. Therefore, the gear mechanism of the device is actuated and one blister pocket (15a) is opened for one dose of the dry powder medicament to be ready for inhalation when the resilient parts (32d, 33d) of the stabilizing resilient covers are pressed on and the mouthpiece cover (2) is switched from the first position to the second position simultaneously. The necessity to press on the resilient parts (32d, 33d) of the stabilizing resilient covers so as to actuate the gear mechanism preclude the consequences which may result from accidental and inadvertent actuations of the gear mechanism.

Figure 4I:
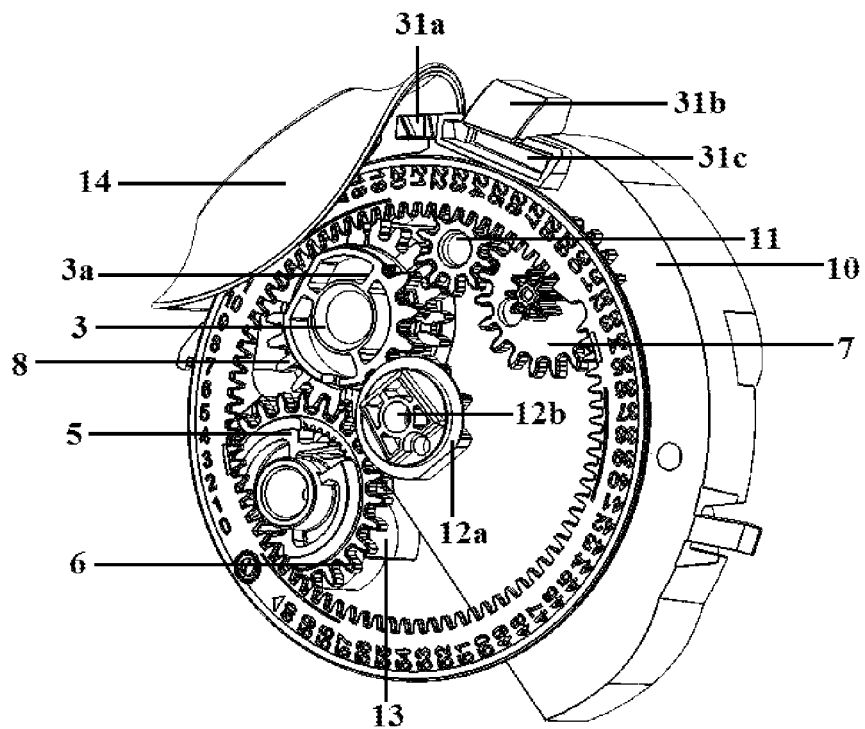
FIGS. 4i and 4j are perspective views of the housing and the gear mechanism of the inhaler of the invention.
Figure 4J:
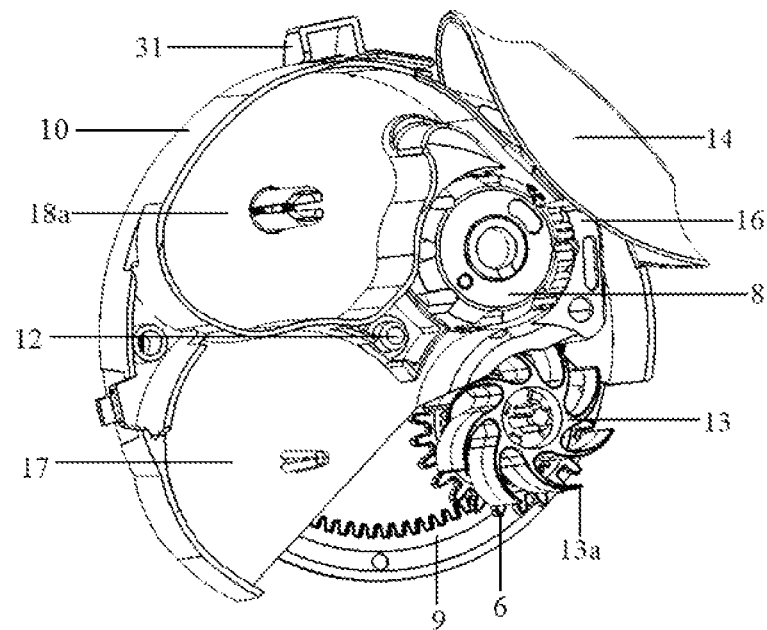
Figure 5D:
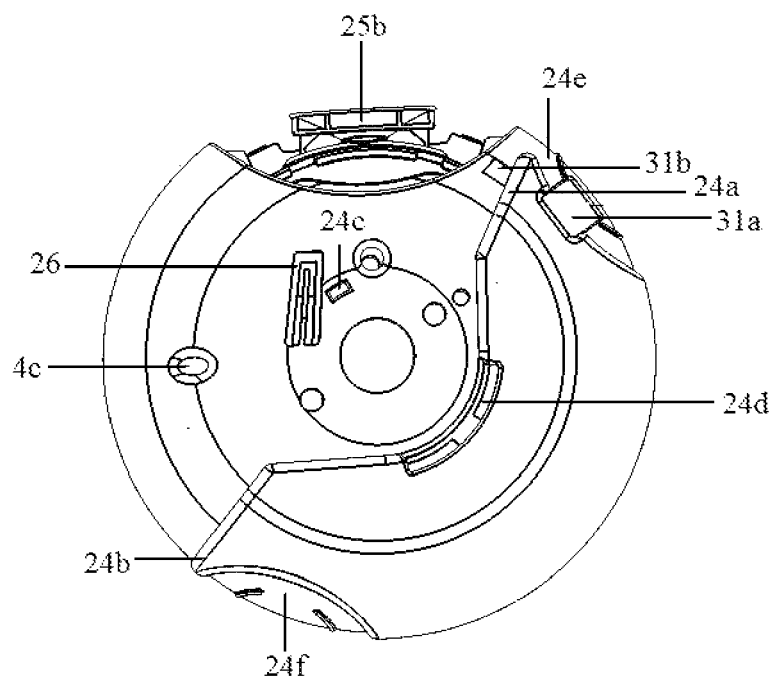
FIG. 5d is another perspective view of the lower housing member of the inhaler of the invention.
Figure 5E:
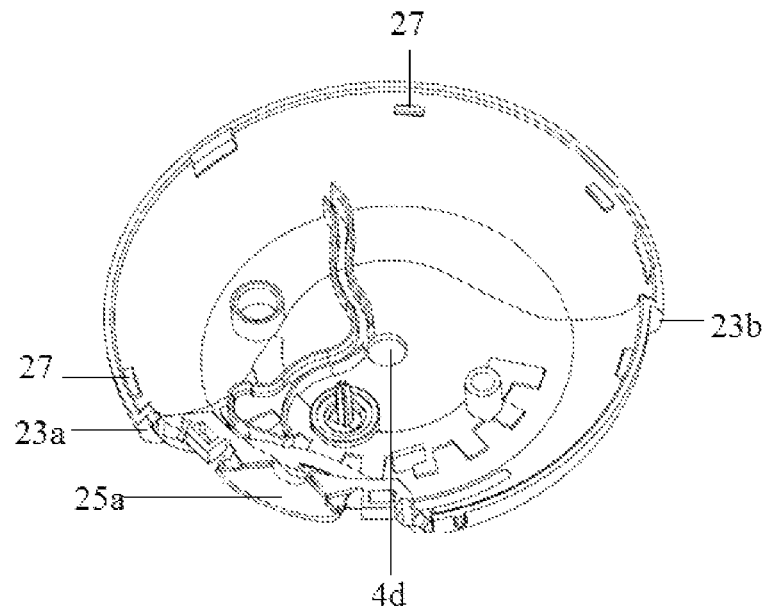
FIGS. 5e and 5f are perspective views of the inner and outer sides of the upper housing member of the inhaler according to the invention, respectively.
Figure 5F:
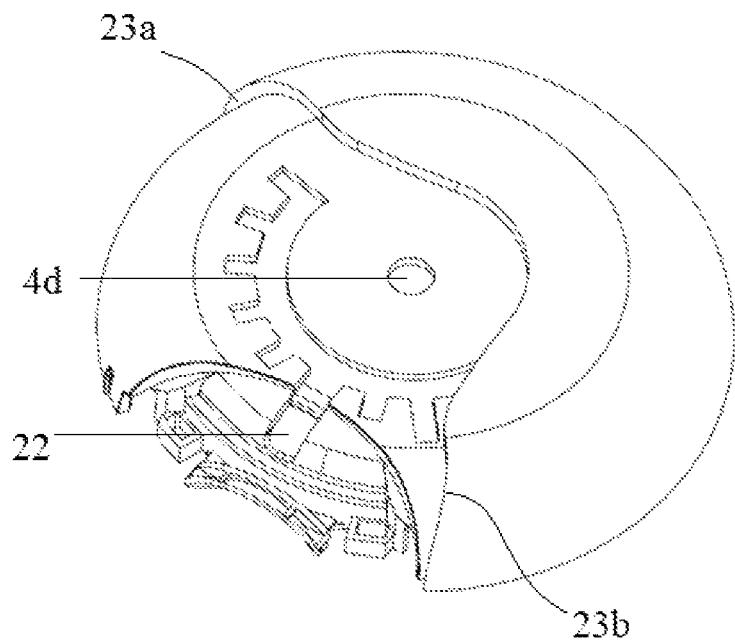
Figure 5G:
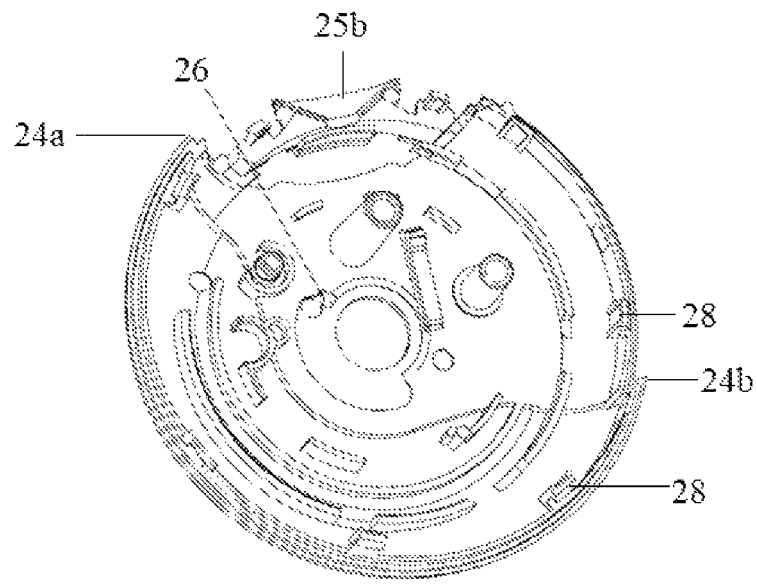
FIGS. 5g and 5h are perspective views of the inner and outer sides of the lower housing member of the inhaler according to the invention, respectively.
Figure 5H:
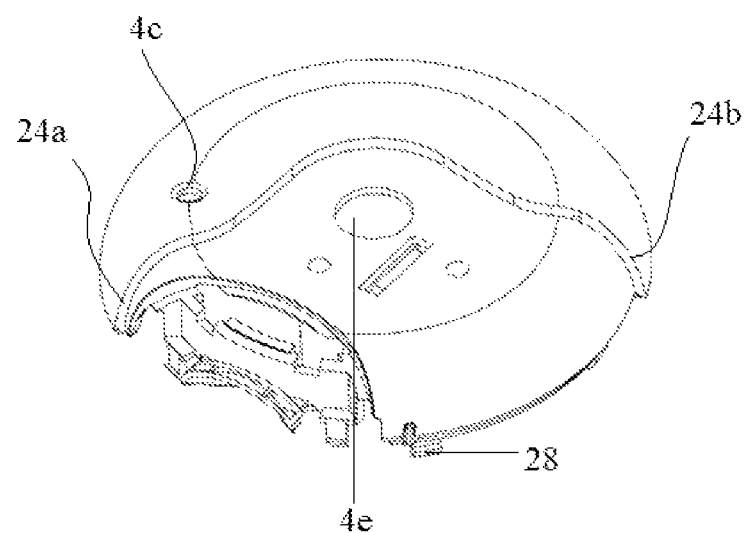
Figure 5I:
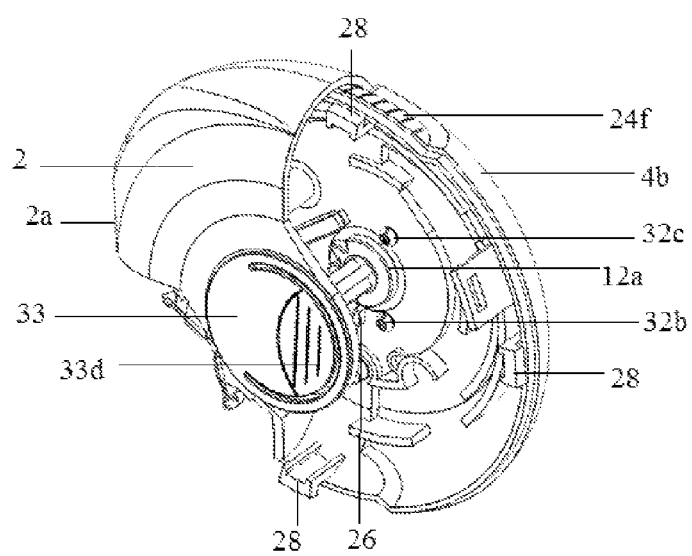
FIG. 5i is a cross-sectional view of the connection of the stabilizing resilient cover with the lower housing member in the inhaler pertaining to the invention.
Figure 10A:
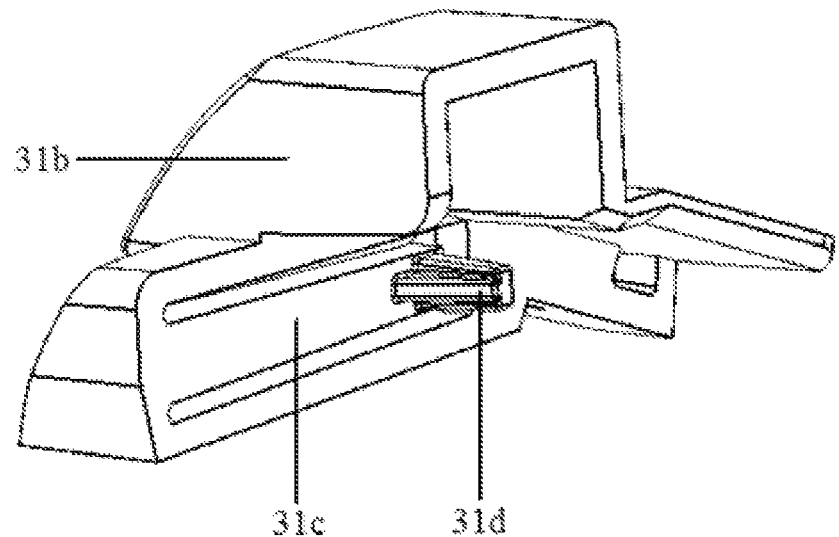
FIGS. 10a and 10b are perspective views of the stopper consisting of the pawl, the pressing button, and the supporting member used in the inhaler of the present invention.
Figure 10B:
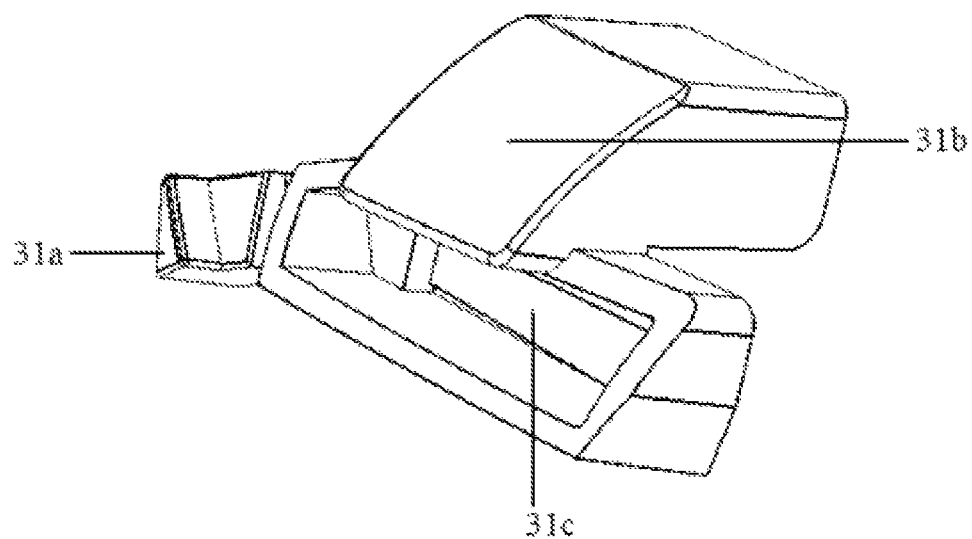

The inhaler (1) of the present invention has a stopper (31) that is situated between the lower housing member (4b) and the housing (10) as engaging with the two holes on the lower housing member (4b) (FIGS. 5d and 6a). The stopper is shown in FIGS. 10a and 10b. This stopper (31) consists of a pawl (31a), a pressing button (31b), and a supporting part (31c). Each of the pawl (31a) and the pressing button (31b) situated in one hole of the lower housing member (4b) and is shown from the outside as the supporting part (31c) is situated at the inside of the inhaler and is not shown from the outside (FIGS. 4i and 6a). For actuation of the inhaler, the mouthpiece cover (2) is switched from the first position to the second position over the rotational path. However, the pawl (32a) is engaged to the recess part (2c) on inside surface of the mouthpiece cover (2) to prevent the movement of the mouthpiece cover (2) when the mouthpiece cover (2) is in the first position in which the mouthpiece (14) is completely covered. Since the pressing button (31b) moves synchronously with the pawl (31a), when the pressing button (31b) is pressed, the pawl (31a) is advanced forward inside of the inhaler and disengaged from the mouthpiece cover (2). After the pawl (31a) is disengaged from the mouthpiece cover (2), the mouthpiece cover (2) can be rotated from the first position to the second position to actuate the inhaler.

Because of the supporting part (31c) of the stopper, there is no need for a spring to enable the pressing button (31b) to be pressed. There is an end (31d) that is integrated with the supporting part and leans the housing of the inhaler. When the pressing button is pressed, the supporting part springs over the end of said supporting part (31d) and both of the pressing button (31b) and the pawl (31a) are advanced forward inside of the inhaler.

Figure 11:
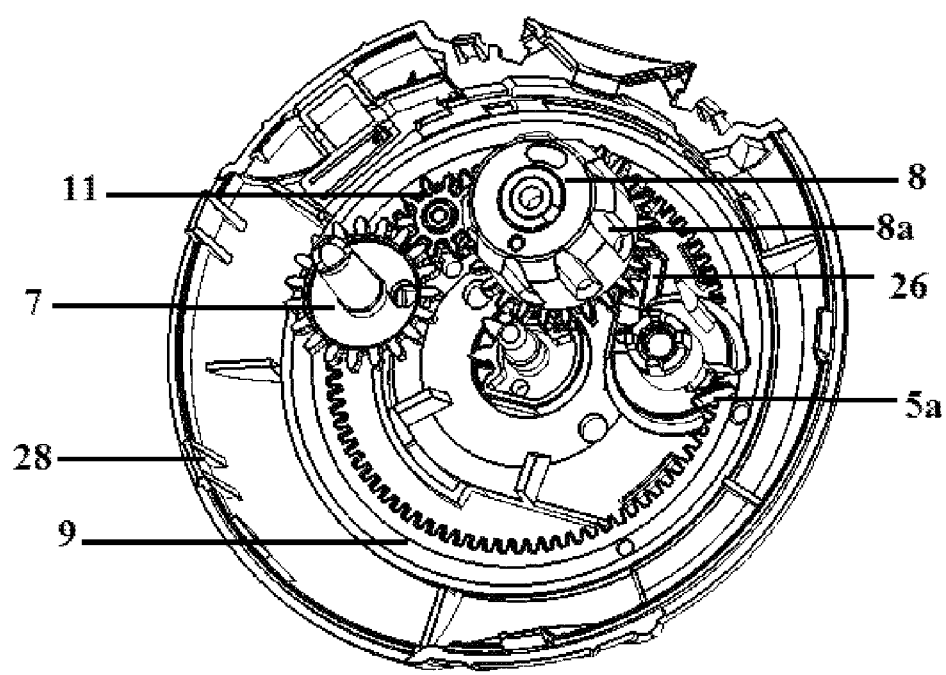
FIG. 11 is a perspective view of the connection between the indexing wheel and another stopper used in the inhaler of the invention.

The inhaler has another stopper (26) in the lower housing member (4b) in order to provide the opened blister in the blister package (15) which is indexed by the indexing wheel (8) to be positioned precisely. FIGS. 7a, 7b, and 11 show that the stopper (26) interlocks with the tooth of the indexing wheel (8) and hinders its rotation. The rotational movement of the mouthpiece cover (2) by the same angle each time the inhaler (1) is actuated is precisely transmitted to the indexing ratchet wheel (3) by the drive gear (12) that joins with one connection point (29) of the mouthpiece cover, and therefore the indexing wheel (8) which engages with the indexing ratchet wheel (3) is rotated by the same angle each time the inhaler (1) is actuated. The stopper (26) positioned in the lower housing member (4b) prevents backward movement of the blister package (15) which is indexed by the indexing wheel (8) that synchronizes with the indexing ratchet wheel (3) by keeping the position of the indexing wheel (8) stable and provides the blister package (15) to be precisely positioned.

As can be seen in FIGS. 7a through 7c, the indexing wheel (8) which synchronizes with the indexing ratchet wheel (3) is engaged with the winding wheel gear (6) and the pinion gear (11) and the rotation of the indexing wheel (8) causes the pinion gear (11) and the winding wheel gear (6) to rotate. Thus, both the peeled lid sheet (15b) of the blister package (15) which is indexed by the rotation of the indexing wheel (8) is tightly coiled on the winding wheel (13) engaging with the winding wheel gear (6) and also the counter gear (9) is provided to be moved by the pinion gear (11) and the base gear (7) as a result of the rotation of the indexing wheel (8).

Figure 9:
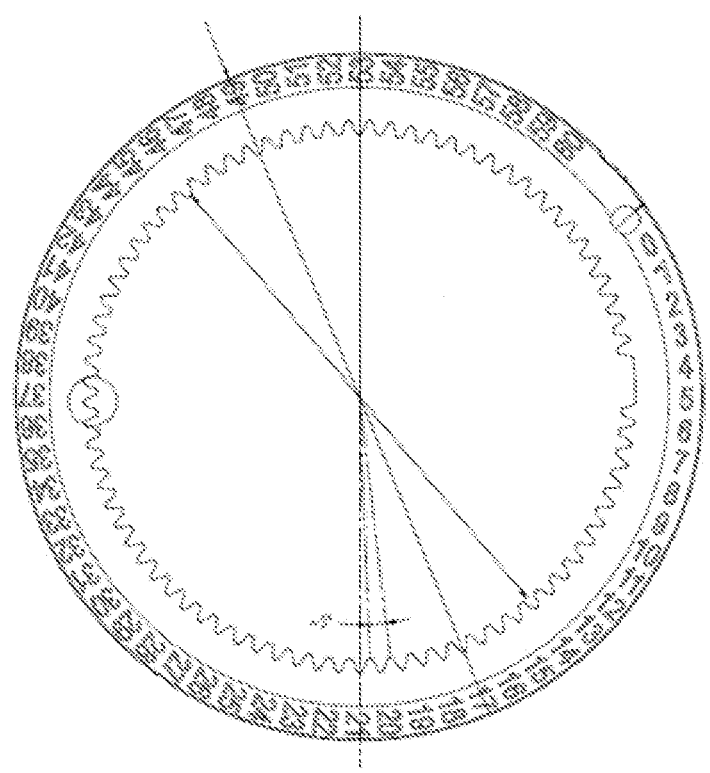
FIG. 9 is a perspective view of the counter gear used in the inhaler according to the present invention.

The rotation of the indexing wheel (8) is transmitted to the base gear (7) engaging with the pinion gear (11) by the pinion gear (11). The small gear which is under the base gear (7) as attached engages with the counter gear (9) (FIG. 7b). Thus, the movement of the indexing wheel (8) is transmitted to the counter gear (9) shown in FIG. 9 by the pinion gear (11) and the base gear. There are numerals incrementing from 1 to 60 in the counter gear displayed in FIG. 9. In response to each actuation of the device, the counter gear rotates approximately 5° and the number of unused blister pockets remained in the device are seen through the display aperture (4c) on the lower housing member (4b).

In use of the device described in FIGS. 1-12, the mouthpiece (14) is exposed when the mouthpiece cover (2) is slid from the first position to the second on the upper housing member (4a) and the lower housing member (4b); the gear mechanism is triggered by the drive gear (12) and one dose of dry powder medicament is prepared for inhalation; the counter gear (9) is indexed and the numeral seen through the display aperture (4c) on the lower housing member (4b) is incremented. After the inhalation is realized, the mouthpiece cover (2) is solely moved from the second position to the first position wherein the mouthpiece (14) is completely covered.

The medicament in dry powder form which is stored in blister cavities is manufactured according to the prior art. According to the present invention, the particle sizes of the active agents comprised in the dry powder medicament are smaller than 20 µm, preferably smaller than 10 µm.

The inhaler pertaining to the present invention has been designed so as to deliver the dry powder medicament used in monotherapy or combined therapy. The term "monotherapy" refers to inhalation treatments in which dry powder medicaments comprising a single active agent are used whereas the term "combined therapy" refers to inhalation treatments in which dry powder medicaments comprising more than one active agents are use used.

The dry powder medicament delivered via the device pertaining to the present invention comprises at least one excipient in addition to the active agent or agents. These excipients are generally chosen from a group comprising monosaccharides (glucose, arabinose, etc.), disaccharides (lactose, saccharose, maltose, etc.), oligo- and polysaccharides (dextran, etc.), polyalcohols (sorbite, mannite, xylite), salts (sodium chloride, calcium carbonate, etc.) or combinations thereof. According to the present invention, the medicament in dry powder form comprises lactose as the excipient. The medicament in dry powder form comprises fine or coarse excipients particles preferably having various particle size ranges in order to deliver the required amount to the lungs.

The active agent or the active agents comprised in the dry powder medicament which is stored in blister packages used in the device pertaining to the present invention can be selected from a group comprising cromolyns, anti-infectives, antihistamines, steroids, anti-inflammatories, bronchodilators, leukotriene inhibitors, PDE IV inhibitors, antitussives, diuretics, anticholinergics, hormones, xanthines and pharmaceutically acceptable combinations thereof.

The active agent comprised in the medicament in dry powder form delivered via the inhaler pertaining to the present invention is preferably selected from a group comprising tiotropium, oxitropium, flutropium, ipratropium, glicopironium, flunisolid, beclomethasone, budesonide, fluticasone, mometasone, ciclesonide, rofleponide, dexamethasone, montelukast, methylcyclopropane acetic acid, sodium cromoglicat, nedocromil sodium, Npropylene, teophylline, roflumilast, ariflo (cilomilast), salmeterol, salbutamol, formoterol, terbutaline, carmoterol, indacaterol, cetirizine, levocetirizine, efletirizine, fexofenadine and their racemates, free base, enantiomers or diastereomers and their pharmaceutically acceptable salts, solvates and/or hydrates or a combination of said active agents.

The device pertaining to the present invention is used in the administration of the medicament in dry powder form which is utilized in the treatment of respiratory diseases, particularly in asthma, chronic obstructive pulmonary disorder (COPD) and allergic rhinitis. Accordingly, the respiratory diseases include, but not restricted to, allergic or non-allergic asthma at any phases, acute lung injury (ALI), acute respiratory distress syndrome (ARDS), exacerbation of airways hyperactivity, bronchiectasis, chronic obstructive pulmonary including emphysema and chronic bronchitis, airways or lung diseases (COPD, COAD or COLD), pneumoconiosis, aluminosis, anthracosis, asbestosis, chalicosis, ptilosis, siderosis, silicosis, tabacosis and byssinosis. The device pertaining to the invention can be used in prophylactic or symptomatic treatment. In addition, the medicament in dry powder form which is preferably used in the symptomatic treatment of allergic asthma and COPD is administered to the patient via the device pertaining to the present invention.

What is claimed is:

1. An inhaler suitable for delivery of a medicament in dry powder form from a blister package comprising a plurality of blister pockets which are spaced at equal intervals, each of which comprises the medicament in dry powder form, the inhaler comprising:

(a) a mouthpiece (14) enabling a patient to inhale the medicament, (b) a gear mechanism enabling the blister package to be indexed and the medicament to become ready for inhalation, (c) a rotatable mouthpiece cover (2) hiding the mouthpiece (14) and triggering the gear mechanism, (d) a drive gear (12) joined with the mouthpiece cover (2) via a connection point of the mouthpiece cover (29), (e) a housing (10) situated between an upper housing member (4*a*) and a lower housing member (4*b*) enclosing the blister package and the gear mechanism, and (f) a stopper (31) for preventing the movement of the mouthpiece cover (2), characterized in that the stopper (31) consists of a pawl (31*a*), a pressing button (31*b*), and a supporting part (31*c*), wherein the pawl (31*a*) is engaged with a recess part (2*c*) on the inside surface of the mouthpiece cover to prevent the movement of the mouthpiece cover (2)

when the mouthpiece cover (2) is in a position in which the mouthpiece (14) is completely covered, and wherein the pressing button (31*b*) moves synchronously with the pawl (31*a*) when pressed to enable the mouthpiece cover (2) to be rotated for actuation of the inhaler as the supporting part (31*c*) is sprung to allow the pressing button (31*b*) to be pressed.

2. The inhaler according to claim 1, wherein the gear mechanism comprises:

(a) the drive gear (12) that actuates the inhaler by transmitting the constant-angle movement of the mouthpiece cover (2) to an indexing ratchet wheel (3);

(b) an indexing wheel (8) which synchronizes with the indexing ratchet wheel (3) and enables the blister package (15) to be indexed in use;

(c) a winding wheel gear (6) which moves a winding wheel (13) via a mechanism gear (5) upon rotation of the indexing wheel (8);

(d) a pinion gear (11) and (e) a base gear (7) that transmit the movement of the indexing wheel (8) to a counter wheel;

(f) a counter gear (9) which displays the number of the unused blister pockets (15*a*) remaining in the inhaler.

3. The inhaler according to claim 2, wherein components (a) through (f) directly or indirectly engage with each other.

4. The inhaler according to claim 1, wherein a restricted path is provided by protrusions (23*a*, 23*b*, 24*a*, 24*b*) on the upper (4*a*) and lower (4*b*) housing members.

5. The inhaler according to claim 4, wherein the mouthpiece cover (2) is rotatable by sliding from a first position to a second position on a rotational path restricted on both ends by protrusion parts (23*a*, 23*b*, 24*a*, 24*b*) on the upper housing member (4*a*) and the lower housing member (4*b*).

6. The inhaler according to claim 5, wherein the mouthpiece cover (2) rotates by a fixed angle in the range of 30° to 160° along a constant-distance path defined by the protrusion parts (23*a*, 23*b*, 24*a*, 24*b*) in response to actuation of the inhaler.

7. The inhaler according to claim 5, wherein a carved part (2*a*) at one end of the mouthpiece cover (2) allows the mouthpiece cover to rotate easily.

8. The inhaler according to claim 1, wherein the gear mechanism is triggered by a rotational movement of the mouthpiece cover (2) from a first position in which the mouthpiece cover (2) resides on protruding parts (23*a*, 24*a*) at one end of a rotational path, wherein the mouthpiece (14) is completely covered and the inhaler is in standby mode to a second position in which the mouthpiece cover resides on protruding parts (23*b*, 24*b*) at the other end of the rotational path, wherein one dose of the medicament is ready for inhalation.

9. The inhaler according to claim 1, wherein the drive gear has two ends and wherein the shape of the end of the drive gear (12*a*) that is connected to the mouthpiece cover (2) is different from the shape of the other end of the drive gear (12*b*).

10. The inhaler according to claim 9, wherein the surface area of the end of drive gear (12*a*) that is connected to the mouthpiece cover (2) is in the range of 30-100 mm$^2$.

11. The inhaler according to claim 10, wherein the surface area is in the range of 32-90 mm$^2$.

12. The inhaler according to claim 11, wherein the surface area is in the range of 40-80 mm$^2$.

13. The inhaler according to claim 9, wherein the shape of the end of drive gear (12*a*) that is connected to the mouthpiece cover (2) is quadrangular or trapezoid.

\* \* \* \* \*